(12) United States Patent
Wirth et al.

(10) Patent No.: US 6,414,030 B1
(45) Date of Patent: Jul. 2, 2002

(54) USE OF BENZENESULFONYL(THIO)UREAS FOR THE TREATMENT AND PROPHYLAXIS OF DYSFUNCTIONS OF THE AUTONOMOUS NERVOUS SYSTEM AND USE OF BENZENESULFONYL(THIO)UREAS IN COMBINATION WITH BETA-RECEPTORS BLOCKERS

(75) Inventors: Klaus Wirth, Kriftel; Heinrich Christian Englert, Hofheim; Helmut Bohn, Schöneck; Heinz Gögelein, Frankfurt am Main; Holger Heitsch, Mainz-Kastel; Uwe Gerlach, Hattersheim, all of (DE)

(73) Assignee: Aventis Pharma Deutschland, GmbH, Frankfurt am Main (DE)

( * ) Notice: Subject to any disclaimer, the term of this patent is extended or adjusted under 35 U.S.C. 154(b) by 0 days.

(21) Appl. No.: 09/986,626

(22) Filed: Nov. 9, 2001

Related U.S. Application Data

(63) Continuation of application No. 09/392,747, filed on Sep. 9, 1999, now abandoned.

(30) Foreign Application Priority Data

Sep. 10, 1998 (DE) .......................................... 198 41 544
Jan. 14, 1999 (DE) .......................................... 199 01 061

(51) Int. Cl.$^7$ ............................................... A61K 31/17
(52) U.S. Cl. ........................ 514/585; 514/586; 514/592; 514/593; 514/821
(58) Field of Search ................................. 514/586, 585, 514/592, 593, 821

(56) References Cited

U.S. PATENT DOCUMENTS

| | | |
|---|---|---|
| 3,426,067 A | 2/1969 | Weber et al. |
| 4,609,672 A | 9/1986 | Koope et al. |
| 5,574,069 A | 11/1996 | Englert et al. |
| 5,652,268 A | 7/1997 | Englert et al. |
| 5,698,696 A | 12/1997 | Englert et al. |
| 5,776,980 A | 7/1998 | Englert et al. |
| 5,985,915 A | 11/1999 | Frangin et al. |

FOREIGN PATENT DOCUMENTS

| | | |
|---|---|---|
| DE | 0151 8874 | 5/1970 |
| EP | 0 612 724 | 8/1994 |
| EP | 0 727 416 | 8/1996 |

OTHER PUBLICATIONS

Olken, N. et al., "$N^G$–Allyl– and $N^G$–Cycloporpyl–L–arginine: Two Novel Inhibitors of Macrophage Nitric Oxide Synthase", J. Med. Chem., vol. 35, pp. 1137–1144 (1992).

Atanassova, I. et al., "The Application of N–Substituted Trichloroacetamides as in situ Isocyanate Generating Reagents for the Synthesis of Acylureas and Sulfonylureas", Synthesis, pp. 734–736 (1987).

Burger, A. et al., "Short– and Long–Term Reproducibility of Heart Rate Variability in Patients With Long–Standing Type I Diabetes Mellitus", Amer. Journal of Cardiology, vol. 80, pp. 1198–1203 (1997).

Vanoli, E. et al., "Vagal Stimulation and Prevention of Sudden Death in Conscious Dogs With a Healed Myocardial Infarction", Circulation Research, vol. 68, pp. 1471–1481 (1991).

Lawson, J. W., "Antiarrhythmic Activity of Some Isoquinoline Derivatives Determined by a Rapid Screening Procedure in the Mouse", J. of Pharmacology and Experimental Therapeutics, vol. 160, pp. 22–31 (1968).

Schwartz, P., "The ATRAMI Prospective Study: Implications for Risk Stratification after Myocardinal Infarction", Cardiac Electrophysiol Review, vol. 2,pp. 38–40 (1998).

Kinugawa, T. et al., "Altered Vagal and Sympathetic Control of Heart Rate in Left Ventricular Dysfunction and Heart Failure", Am. J. Physiol., vol. 268, pp. R310–R316 (1995).

Gennaro, A. R., "Remington's Pharmaceutical Sciences", $17^{th}$ Ed., pp. 1418–1419 (1985).

Hjalmarson et al., "The Role of β–Blockers in Left Ventricular Dysfuction and Heart Failure" Drugs, vol. 54, pp. 501–510 (1997.

Feuerstein et al., "Carvedilol, a novel vasodilating beta–blocker with the potential for cardiovasculary organ protection", Eur. Heart J., vol. 17, svpp. B; pp. 24–29 (1996).

(List continued on next page.)

Primary Examiner—James H. Reamer
(74) Attorney, Agent, or Firm—Finnegan, Henderson, Farabow, Garrett & Dunner, LLP

(57) ABSTRACT

Substituted benzenesulfonylureas and -thioureas of the formula I in which $R^1$, $R^2$, E, X, Y and Z have the meanings described herein, show effects on the autonomous nervous system. The invention relates to the use of the compounds of the formula I in the treatment and prophylaxis of dysfunctions of the autonomous nervous system, in particular of vagal dysfunctions, for example in the case of cardiovascular diseases. The invention also relates to the use of compounds of the formula I in combination with beta-receptor blockers and to products and pharmaceutical preparations which comprise at least one compound of the formula I and at least one beta-receptor blocker, and to novel compounds.

30 Claims, No Drawings

OTHER PUBLICATIONS

Gogelein et al., "HMR 1883, a Novel Cardioselective Inhibitor of the ATP–Sensitive Potassium Channel. Part I: Effects on Cardiomyocytes, Coronary Flow and Pancreatic β–Cells", J. Pharm. and Exp. Therapeutics, vol. 286; pp. 1453–1464 (1996).

Billman et al., "HMR 1883, a Novel Cardioselective Inhibitor of the ATP–Sensitive Potassium Channel. Part II: Effects on Susceptibility to Ventricular Fibrillation Induced by Myocardial Ischemia in Conscious Dogs", J. Pharm. and Exp. Therapeutics, vol. 286, pp. 1465–1473 (1998).

Bohn et al., "The KATP Channel Blocker HMR 1883 Attenuates the Effects of Ischaemia on Map Duration and Improves Survival During Lab Occlusion in the Anaesthetised Pig", British J. of Pharmacology, vol. 24, p. 24P (1998).

Kardos et al., "Lipophilic versus hydrophilic $β^1$ blockers and the cardiac sympatho–vagal balance during stress and daily activity in patients after acute myocardial infarction", Heart, vol. 79, pp. 153–160 (1998).

Frey et al., "Erhöhung der vagalen Aktivität nach Gabe des Kalziumantagonisten Diltiazem bei Patienten mit koronarer Herzkrankheit", Zeitschrift fur Kandiologie, vol. 84, pp. 105–111 (1995).

Aumueller et al., "Benzenesulfonylureas", Chemical Abstract, vol. 82, No. 43073m (1975).

Derwent Abstract of DE 1518874.

USE OF BENZENESULFONYL(THIO)UREAS FOR THE TREATMENT AND PROPHYLAXIS OF DYSFUNCTIONS OF THE AUTONOMOUS NERVOUS SYSTEM AND USE OF BENZENESULFONYL(THIO)UREAS IN COMBINATION WITH BETA-RECEPTORS BLOCKERS

This application is a continuation of application Ser. No. 09/392,747, filed Sep. 9, 1999, now abandoned.

Use of benzenesulfonyl(thio)ureas for the treatment and prophylaxis of dysfunctions of the autonomous nervous system and use of benzenesulfonyl(thio)ureas in combination with beta-receptor blockers.

This application claims the benefit of priority to German patent applications serial No. 19841534.6, filed Sep. 10, 1998, and serial No. 19901061.7, filed Jan. 14, 1999. Both applications are incorporated by reference herein.

Substituted benzenesulfonylureas and -thioureas of the formula I

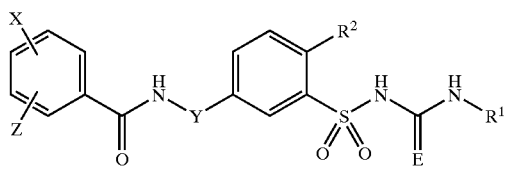

in which $R^1$, $R^2$, E, X, Y and Z have the meanings given below, show effects on the autonomous nervous system. The invention relates to the use of the compounds of the formula I in the treatment and prophylaxis of dysfunctions of the autonomous nervous system, in particular of vagal dysfunctions, for example in the case of cardiovascular diseases, and to their use for preparing medicaments for such treatment and prophylaxis. Furthermore, the invention relates to the use of compounds of the formula I in combination with beta-receptor blockers and to products and pharmaceutical preparations which comprise at least one compound of the formula I and at least one beta-receptor blocker, and to novel compounds.

Compounds of the formula I are known from U.S. Pat. No. 5,574,069 (EP-A-612 724), U.S. Pat. No. 5,776,980, U.S. Pat. No. 5,698,596, and U.S. Pat. No. 5,652,268 (EP-A-727 416), which are incorporated herein by reference and the content of which is part of the present disclosure. In these publications it is described that compounds of the formula I inhibit ATP-sensitive potassium channels in particular at the heart, and that they have direct antiarrhythmic action by influencing the action potential duration of the heart which is a result of the direct effect on the electrical properties of heart muscle cells. Owing to this property, the compounds of the formula I are suitable, for example, for treating ventricular fibrillation and other cardiac arrhythmias. Other pharmacological effects of the compounds of the formula I have hitherto not been described. Surprisingly, it has now been found that the compounds of the formula I also have an effect on the peripheral and/or the central autonomous nervous system. In particular, they influence the vagal nervous system and have a stimulating effect on the vagal nervous system.

In an ideal case, an optimum cooperation, adapted to the particular situation, exists between the sympathetic (=stimulating) nervous system and the vagal (or parasympathetic) (=depressing) nervous system. In the case of a disease, however, this cooperation can be disturbed and a dysfunction of the autonomous nervous system may be present, i.e. an imbalance between the activity of the vagal nervous system and the activity of the sympathetic nervous system. Sympathovagal imbalance is generally understood as an overactivity of the sympathetic (=stimulating) nervous system and/or an impaired function of the vagal (=depressing) nervous system, where the two parts of the nervous system may mutually influence each other. In particular, it is known that an impaired function of the vagal system may result in overactivity of the sympathetic system. To avoid damage to cells or organs of the body by overshooting biological or biochemical processes which are stimulated by excessive activity of the sympathetic nervous system, it is therefore attempted in such cases to balance out a sympathovagal imbalance, for example to reestablish normal vagal activity by treating a vagal dysfunction or impaired function.

Examples of diseases where elimination of a harmful sympathovagal imbalance by treatment of a vagal dysfunction is suitable are organic heart diseases, for example coronary heart disease, cardiac insufficiency and cardiomyopathies. Damage to the health which result from an imbalance of the autonomous nervous system when the dysfunction affects the heart are, for example, weakening of the strength of the heart or sometimes fatal cardiac arrhythmias. The significance of the autonomous nervous system for sudden cardiac death in cases of heart diseases has been described, for example, by P. J. Schwartz (The ATRAMI prospective study: implications for risk stratification after myocardial infarction; Cardiac Electrophysiology Review 1998, 2, 38–40) or T. Kinugawa et al. (Altered vagal and sympathetic control of heart rate in left ventricular dysfunction and heart failure; Am. J. Physiol. 1995, 268, R310–316). Experimental investigations with electric stimulation of the vagus of the heart or stimulating analogs of the vagal transmitter acetylcholine, for example carbachol, support the protective effect of vagal activation against fatal cardiac arrhythmias (see, for example, E. Vanoli et al., Vagal stimulation and prevention of sudden death in conscious dogs with a healed myocardial infarction; Circ. Res. 1991, 68(5), 1471–81).

However, sympathovagal imbalance can also occur, for example, as a consequence of a metabolic disorder, for example diabetes mellitus, (see, for example, A. J. Burger et al., Short- and long-term reproducibility of heart rate variability in patients with long-standing type I diabetes mellitus; Am. J. Cardiol. 1997, 80, 1198–1202). Impaired function of the vagal system may also be temporary, for example in cases of oxygen deficit of, for example, the heart, resulting in a reduced secretion of vagal neurotransmitters, for example acetylcholine.

Owing to the surprising capacity of the compounds of the formula I to mend an impaired function of the vagal system, or to reestablish normal vagal activity, these compounds offer an efficient possibility to reduce, to eliminate or to prevent dysfunctions of the autonomous nervous system and their consequences such as, for example, the abovementioned diseases. Thus, a subject of the present invention is the use of benzenesulfonyl(thio)ureas of the formula I

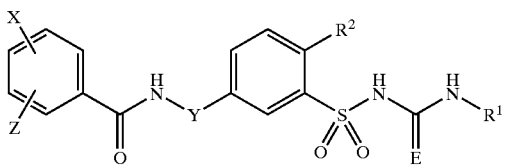

in which
- R$^1$ is hydrogen, methyl or trifluoromethyl;
- R$^2$ is hydrogen, halogen, (C$_1$–C$_6$)-alkyl, (C$_1$–C$_6$)-alkoxy, (C$_1$–C$_6$)-alkoxy-(C$_1$–C$_4$)-alkoxy-, (C$_1$–C$_6$)-alkoxy-(C$_1$–C$_4$)-alkoxy-(C$_1$–C$_4$)-alkoxy-, (C$_1$–C$_6$)-alkylthio, (C$_1$–C$_6$)-fluoroalkoxy or (C$_1$–C$_6$)-fluoroalkyl;
- E is oxygen or sulfur;
- Y is a hydrocarbon residue of the formula —(CR$^3{}_2$)$_n$— in which the residues R$^3$ independently of one another are each hydrogen or (C$_1$–C$_2$)-alkyl and n is 1, 2, 3 or 4;
- X is hydrogen, halogen or (C$_1$–C$_6$)-alkyl;
- Z is halogen, nitro, (C$_1$–C$_4$)-alkoxy or (C$_1$–C$_4$)-alkyl;

in all their stereoisomeric forms and mixtures thereof in all ratios, and/or their physiologically acceptable salts for preparing a medicament for the treatment or prophylaxis of a dysfunction of the autonomous nervous system.

Alkyl is a straight-chain, branched or cyclic saturated hydrocarbon residue. This also applies if the alkyl residue is substituted, such as, for example, in fluoroalkyl residues, or is present as a substituent in another residue, for example in alkoxy residues, alkylthio residues or fluoroalkoxy residues. Examples of straight-chain or branched alkyl residues are methyl, ethyl, n-propyl, isopropyl, n-butyl, sec-butyl, isobutyl, tert-butyl, n-pentyl, isopentyl, neopentyl, n-hexyl or isohexyl. Examples of cyclic alkyl residues, which, according to their nature, must have at least three carbon atoms, are cyclopropyl, cyclobutyl, cyclopentyl or cyclohexyl. Cyclic alkyl residues may additionally carry one or more, for example 1, 2, 3 or 4, (C$_1$–C$_4$)-alkyl residues or (C$_1$–C$_4$)-fluoroalkyl residues, for example methyl groups or trifluoromethyl groups.

Examples of the residue alkoxy (=alkyloxy), which is attached via an oxygen atom, are methoxy, ethoxy, n-propoxy, isopropoxy, n-butoxy, isobutoxy, tert-butoxy, n-pentoxy, neopentoxy, isohexoxy, cyclopropoxy, cyclobutoxy, cyclopentoxy or cyclohexoxy. Examples of the residue alkylthio, which is attached via a sulfur atom, are methylthio, ethylthio, n-propylthio, isopropylthio, n-butylthio, isobutylthio, tert-butylthio, n-pentylthio, neopentylthio, isohexylthio, cyclopropylthio, cyclobutylthio, cyclopentylthio or cyclohexylthio.

Fluoroalkyl is an alkyl residue in which one or more hydrogen atoms of an alkyl residue which is as defined above are replaced by fluorine atoms. A fluoroalkyl residue may contain one or more fluorine atoms, for example 1, 2, 3, 4, 5, 6 or 7. At most, all hydrogen atoms may have been exchanged, i.e. perfluorosubstitution is present. Examples of fluoroalkyl are trifluoromethyl, 2,2,2-trifluoroethyl or pentafluoroethyl. Fluoroalkoxy is an alkoxy residue as defined above in which, as illustrated above, one or more hydrogen atoms are replaced by fluorine atoms.

For all alkyl groups in the residues alkoxy-alkoxy- and alkoxy-alkoxy-alkoxy-, which are attached via an oxygen atom, the above definitions and illustrations apply independently of one another. In the divalent alkyl groups contained in these groups, the two free bonds via which these groups are attached to the neighboring groups, can be in any positions, for example in the 1,1-position of an alkyl residue, in the 1,2-position, in the 1,3-position or 1,4-position. Examples of such divalent residues are methylene, 1,2-ethylene, 1,2-propylene, 1,3-propylene, 1,4-butylene or 2,2-dimethyl-1,3-propylene. A preferred divalent residue of this type is 1,2-ethylene. Examples of alkoxy-alkoxy- residues are methoxymethoxy, 2-methoxyethoxy, 3-methoxypropoxy, 4-methoxybutoxy, 6-methoxyhexoxy, 2-ethoxyethoxy, 2-ethoxy-2-methylethoxy, 3-ethoxypropoxy, 2-isobutoxyethoxy, 2-tert-butoxyethoxy, 2-cyclopropoxyethoxy, 2-cyclopentoxyethoxy. Examples of alkoxy-alkoxy-alkoxy-residues are (2-methoxyethoxy)methoxy, 2-(2-methoxyethoxy)ethoxy, 2-(2-isopropoxyethoxy)ethoxy, 2-(2-n-butoxyethoxy)ethoxy, 2-(2-cyclopropoxyethoxy)ethoxy, 3-(2-methoxyethoxy)propoxy, 2-(2-methoxy-2-methylethoxy)-2-methylethoxy.

Examples of halogen are fluorine, chlorine, bromine and iodine, in particular fluorine and chlorine.

The present invention embraces all stereoisomeric forms of the compounds of the formula I. Asymmetric centers contained in the compounds of the formula I, for example in the group Y, can each, independently of one another, have the S configuration or the R configuration. The invention includes all possible enantiomers and diastereomers, and also mixtures of two or more stereoisomeric forms, for example mixtures of enantiomers and/or diastereomers, in all ratios. The invention provides the enantiomers therefore in enantiomerically pure form, both as levorotatory and as dextrorotatory antipodes, in the form of racemates and in the form of mixtures of the two enantiomers in all ratios. The invention provides diastereomers both in pure form and in the form of mixtures of two or more diastereomers in all quantity ratios. Meso compounds, for example, are also included. If a cis/trans isomerism is present, the invention provides both the cis form and the trans form and mixtures of these forms in all ratios. The individual stereoisomers can be prepared, if desired, by separating a mixture according to customary methods, for example by chromatography or crystallization, or by using stereochemically uniform starting materials in the synthesis. If appropriate, derivatization may be carried out prior to a separation of stereoisomers. A mixture of stereoisomers can be separated at the stage of the compounds of the formula I or at the stage of an intermediate in the course of the synthesis. The invention also includes all tautomeric forms of the compounds of the formula I.

Physiologically acceptable salts of the compounds of the formula I are in particular pharmaceutically utilizable salts or non-toxic salts. They may contain inorganic or organic salt components (see also Remington's Pharmaceutical Sciences (A. R. Gennaro (Editor), Mack Publishing Co., Easton Pa., 17$^{th}$ edition, page 1418 (1985)). Such salts can be prepared, for example, from compounds of the formula I with suitable inorganic or organic bases, for example with alkali metal or alkaline earth metal compounds, such as sodium hydroxide or potassium hydroxide, or with ammonia or organic amino compounds or ammonium hydroxides. Reactions of compounds of the formula I with bases for preparing the salts are generally carried out in accordance with customary procedures in a solvent or diluent. Salts which are advantageous owing to their physiological and chemical stability are in many cases sodium, potassium, magnesium or calcium salts or ammonium salts, in particular sodium salts. Salt formation at the nitrogen atom of the (thio)urea group which is attached to the sulfonyl group leads to compounds of the formula II

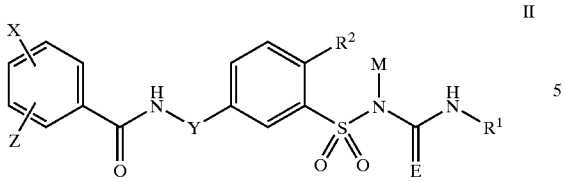

II

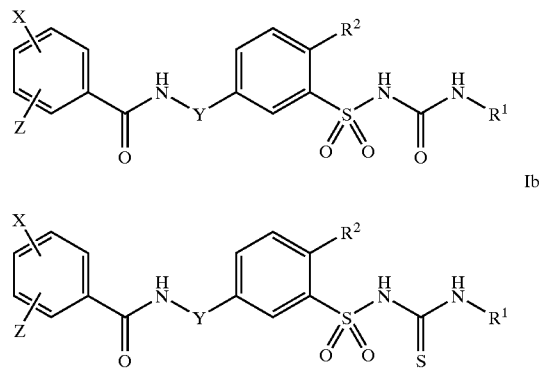

Ia

Ib in which $R^1$, $R^2$, E, X, Y and Z have the meanings given above and the cation M is, for example, an alkali metal ion or an equivalent of an alkaline earth metal ion, for example the sodium, potassium, magnesium or calcium ion, or is the unsubstituted ammonium ion or an ammonium ion having one or more organic residues. An ammonium ion representing M can, for example, also be the cation obtained by protonation from an amino acid, in particular a basic amino acid, such as, for example, lysine or arginine.

The present invention also includes all solvates of compounds of the formula I and their physiologically acceptable salts, for example hydrates or adducts with alcohols, and also derivatives of compounds of the formula I and prodrugs and active metabolites.

In the formula I $R^1$ is preferably hydrogen or methyl, particularly preferably methyl.

If $R^2$ in the formula I is halogen, the residue is preferably chlorine or fluorine. If $R^2$ in the formula I is $(C_1-C_6)$-alkyl, the residue is preferably $(C_1-C_4)$-alkyl, in particular methyl. If $R^2$ in the formula I is $(C_1-C_6)$-alkoxy, the residue is preferably $(C_1-C_6)$-alkoxy, in particular methoxy. If $R^2$ in the formula I is $(C_1-C_6)$-alkoxy-$(C_1-C_4)$-alkoxy-, the residue is preferably $(C_1-_4)$-alkoxy-$(C_1-C_4)$-alkoxy-, in particular 2-(($C_1-C_4$)-alkoxy)ethoxy-, specifically 2-methoxyethoxy-. If $R^2$ in the formula I is $(C_1-C_6)$-alkoxy-$(C_1-C4)$-alkoxy-$(C_1-C_4)$-alkoxy-, the residue is preferably $(C_1-C_4)$-alkoxy-$(C_1-C_4)$-alkoxy-$(C_1-C_4)$-alkoxy-, in particular 2-(2-(($C_1-C_4$)-alkoxy)ethoxy)ethoxy-, specifically 2-(2-methoxyethoxy)ethoxy-. A group of preferred residues $R^2$ is formed by the residues $(C_1-C_6)$-alkyl, $(C_1-C_6)$-alkoxy and $(C_1-C_6)$-alkoxy-$(C_1-C_4)$-alkoxy-, in particular the residues $(C_1-C_6)$-alkoxy and $(C_1-C_6)$-alkoxy-$(C_1-C_4)$-alkoxy-, specifically the residues methoxy and 2-methoxyethoxy-.

The residues $R^3$ independently of one another are preferably hydrogen or methyl, particularly preferably hydrogen. n is preferably 2 or 3. The group Y preferably contains up to four carbon atoms. Particularly preferably, Y is the group $-(CH_2)_n-$, where n is 2 or 3, or the group $-CHR^3-CH_2-$, in which $R^3$ is methyl or ethyl and the group $-CHR^3-$ is attached to the NH group. Very particularly preferably, Y is the group $-CH_2-CH_2-$.

X is preferably halogen or $(C_3-C_6)$-alkyl, for example fluorine, chlorine, n-propyl, isopropyl, n-butyl, isobutyl, sec-butyl, tert-butyl, tert-amyl or 1,1-dimethylpropyl, in particular chlorine or tert-butyl. Z is preferably halogen, nitro, $(C_1-C_4)$-alkoxy or $(C_1-C_4)$-alkyl, particularly preferably $(C_1-C_4)$-alkoxy, for example methoxy. The residues X and Z can be in any position of the phenyl residue to which they are attached. Preferably, X is attached in the 5-position and Z in the 2-position of the phenyl residue, in each case relative to the group C(=O)—NH in the 1-position.

If in the compounds of the formula I according to the invention the group E is oxygen, ureas of the formula Ia are present. If E is sulfur, thioureas of the formula Ib are present. E is preferably sulfur.

Preferred compounds of the formula I for the use according to the invention are compounds in which one or more of the residues have preferred meanings, all combinations of preferred meanings being a subject of the present invention.

For example, preference is given to the use of compounds of the formula I in which $R^1$ is hydrogen, methyl or trifluoromethyl;

$R^2$ is hydrogen, halogen, $(C_1-C_6)$-alkyl, $(C_1-C_6)$-alkoxy, $(C_1-C_4)$-alkoxy-$(C_1-C_4)$-alkoxy-, $(C_1-C_4)$-alkoxy-$(C_1-C_4)$-alkoxy-$(C_1-C_4)$-alkoxy-, $(C_1-C_6)$-alkylthio, $(C_{1-C6})$-fluoroalkoxy or $(C_1-C_6)$-fluoroalkyl;

E is oxygen or sulfur;

Y is a hydrocarbon residue of the formula $-(CR^3{}_2)_n-$ in which the residues $R^3$ independently of one another are each hydrogen or $(C_1-C_2)$-alkyl and n is 1, 2, 3 or 4;

X is halogen or $(C_3-C_6)$-alkyl;

Z is halogen, nitro, $(C_1-C_4)$-alkoxy or $(C_1-C_4)$-alkyl;

in all their stereoisomeric forms and mixtures thereof in all ratios, and/or their physiologically acceptable salts.

Particular preference is given to the use of compounds of the formula I in which $R^1$ is hydrogen or methyl;

$R^2$ is hydrogen, halogen, $(C_1-C_6)$-alkyl, $(C_1-C_6)$-alkoxy, $(C_1-C_4)$-alkoxy-$(C_1-C_4)$-alkoxy-, $(C_1-C_4)$-alkoxy-$(C_1-C_4)$-alkoxy-$(C_1-C_4)$-alkoxy-, $(C_1-C_6)$-alkylthio, $(C_{1-C6})$-fluoroalkoxy or $(C_1-C_6)$-fluoroalkyl;

E is oxygen or sulfur;

Y is a hydrocarbon residue of the formula $-(CR^3{}_2)_n-$ in which the residues $R^3$ independently of one another are each hydrogen or methyl and n is 1, 2, 3 or 4;

X is halogen or $(C_3-C_6)$-alkyl;

Z is $(C_1-C_4)$-alkoxy;

in all their stereoisomeric forms and mixtures thereof in all ratios, and/or their physiologically acceptable salts.

More particular preference is given to the use of compounds of the formula I in which $R^1$ is hydrogen or methyl;

$R^2$ is hydrogen or halogen;

E is oxygen or sulfur;

Y is a hydrocarbon residue of the formula $-(CR^3{}_2)_n-$ in which the residues $R^3$ independently of one another are each hydrogen or methyl and n is 1, 2, 3 or 4;

X is halogen or $(C_3-C_6)$-alkyl;

Z is $(C_1-C_4)$-alkoxy;

in all their stereoisomeric forms and mixtures thereof in all ratios, and/or their physiologically acceptable salts.

More particular preference is also given to the use of compounds of the formula I in which R$^1$ is hydrogen or methyl;

R$^2$ is (C$_1$–C$_6$)-alkylthio, (C$_1$–C$_6$)-fluoroalkoxy or (C$_1$–C$_6$)-fluoroalkyl;

E is oxygen or sulfur;

Y is a hydrocarbon residue of the formula —(CR$^3$$_2$)$_n$— in which the residues R$^3$ independently of one another are each hydrogen or methyl and n is 1, 2, 3 or 4;

X is halogen or (C$_3$–C$_6$)-alkyl;

Z is (C$_1$–C$_4$)-alkoxy;

in all their stereoisomeric forms and mixtures thereof in all ratios, and/or their physiologically acceptable salts.

More particular preference is furthermore also given to the use of compounds of the formula I in which R$^1$ is hydrogen or methyl;

R$^2$ is (C$_1$–C$_6$)-alkyl, (C$_1$–C$_6$)-alkoxy, (C$_1$–C$_4$)-alkoxy-(C$_1$–C$_4$)-alkoxy- or (C$_1$–C$_4$-alkoxy-(C$_1$–C$_4$)-alkoxy-(C$_1$–C$_4$)-alkoxy-;

E is oxygen or sulfur;

Y is a hydrocarbon residue of the formula —(CR$^3$$_2$)$_n$— in which the residues R$^3$ independently of one another are each hydrogen or methyl and n is 1, 2, 3 or 4;

X is halogen or (C$_3$–C$_6$)-alkyl;

Z is (C$_1$–C$_4$)-alkoxy;

in all their stereoisomeric forms and mixtures thereof in all ratios, and/or their physiologically acceptable salts.

Very particular preference is given to the use of compounds of the formula I in which R$^1$ is hydrogen or methyl;

R$^2$ is methyl, methoxy or 2-methoxyethoxy-;

E is oxygen or sulfur;

Y is a hydrocarbon residue of the formula —(CR$^3$$_2$)$_n$— in which the residues R$^3$ independently of one another are each hydrogen or methyl and n is 2 or 3;

X is halogen or (C$_3$–C$_6$)-alkyl;

Z is (C$_1$–C$_4$)-alkoxy;

in all their stereoisomeric forms and mixtures thereof in all ratios, and/or their physiologically acceptable salts.

Specific preference is given to the use of compounds of the formula I in which

R$^1$ is methyl;

R$^2$ is methyl, methoxy or 2-methoxyethoxy;

E is sulfur;

Y is a hydrocarbon residue of the formula —(CH$_2$)$_n$— in which n is 2 or 3;

X is halogen or (C$_3$–C$_6$)-alkyl;

Z is (C$_1$–C$_4$)-alkoxy;

in all their stereoisomeric forms and mixtures thereof in all ratios, and/or their physiologically acceptable salts.

The compounds of the formula I according to the invention can be prepared, for example, by the processes below.

(a) Aromatic sulfonamides of the formula III or their salts of the formula IV can be reacted with R$^1$-substituted isocyanates of the formula V to give substituted benzenesulfonylureas of the formula Ia

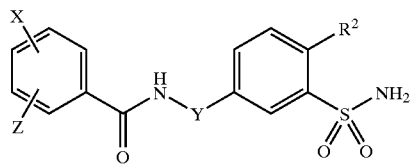

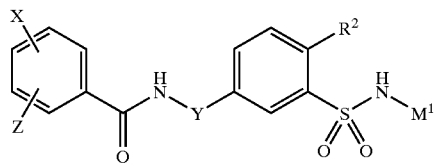

Suitable cations M$^1$ in the salts of the formula IV are alkali metal ions or alkaline earth metal ions such as, for example, sodium ions or potassium ions, or ammonium ions such as, for example, tetraalkylammonium ions. Equivalent to the R$^1$-substituted isocyanates of the formula V, it is possible to use R$^1$-substituted carbamic acid esters, R$^1$-substituted carbamoyl halides or R$^1$-substituted ureas.

(b) Benzenesulfonylureas of the formula Ia which are unsubstituted at the urea group and in which R$^1$ is hydrogen, can be prepared by reacting aromatic benzenesulfonamides of the formula III or their salts of the formula IV with trialkylsilyl isocyanates, such as trimethylsilyl isocyanate, or with silicon tetraisocyanate and hydrolysis of the silicon-substituted benzenesulfonylureas which are primarily formed. Furthermore, compounds of the formula Ia in which R$^1$ is hydrogen can be obtained from benzenesulfonamides of the formula III or their salts of the formula IV by reaction with halogen cyanides and hydrolysis of the N-cyanosulfonamides which are primarily formed with mineral acids at temperatures between 0° C. and 100° C.

(c) Benzenesulfonylureas of the formula Ia can be prepared from aromatic benzenesulfonamides of the formula III or their salts of the formula IV using R$^1$-substituted trichloroacetamides of the formula VI in the presence of a base in an inert solvent according to Synthesis 1987, 734–735 at temperatures between 25° C. and 150° C.

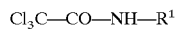

Suitable bases are, for example, alkali metal or alkaline earth metal hydroxides, hydrides, amides or alkoxides, such as sodium hydroxide, potassium hydroxide, calcium hydroxide, sodium hydride, potassium hydride, calcium hydride, sodium amide, potassium amide, sodium methoxide, sodium ethoxide, potassium methoxide or potassium ethoxide. Suitable inert solvents are ethers, such as tetrahydrofuran, dioxane or ethylene glycol dimethyl ether (DME), ketones, such as acetone or butanone, nitriles, such as acetonitrile, nitro compounds, such as nitromethane, esters, such as ethyl acetate, amides, such as dimethylformamide (DMF) or N-methylpyrrolidone (NMP), hexamethylphosphoric triamide, sulfoxides, such as dimethyl sulfoxide (DMSO), sulfones, such as sulfolane, hydrocarbons, such as benzene, toluene, xylenes. Moreover, mixtures of these solvents with one another are also suitable.

(d) Benzenesulfonylthioureas of the formula Ib can be prepared from benzenesulfonamides of the formula III or their salts of the formula IV and R$^1$-substituted isothiocyanates of the formula VII.

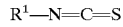

Benzenesulfonylthioureas of the formula Ib which are unsubstituted at the thiourea group and in which $R^1$ is hydrogen, can be prepared by reacting aromatic benzenesulfonamides of the formula III or their salts of the formula IV with trialkylsilyl isothiocyanates, such as trimethylsilyl isothiocyanate, or with silicon tetraisothiocyanate and hydrolysis of the silicon-substituted benzenesulfonylthioureas which are primarily formed. Furthermore, it is possible to prepare compounds of the formula Ib in which $R^1$ is hydrogen by reacting aromatic benzenesulfonamides of the formula III or their salts of the formula IV with benzoyl isothiocyanate and subsequently reacting the benzoyl-substituted benzenesulfonylthiourea intermediates with aqueous mineral acids. Similar processes are described in J. Med. Chem. 1992, 35, 1137–1144.

(e) Substituted benzenesulfonylureas of the formula Ia can be prepared by conversion reactions from benzenesulfonylthioureas of the formula Ib. Desulfurization, i.e. replacement of the sulfur atom in the corresponding benzenesulfonylthiourea by an oxygen atom, can be carried out, for example, with the aid of oxides or salts of heavy metals or by using oxidizing agents, such as hydrogen peroxide, sodium peroxide or nitrous acid. Thioureas can also be desulfurized by treatment with phosgene or phosphorus pentachloride. Chloroformic acid amidines or carbodiimides are obtained as intermediate compounds and can be converted into the corresponding substituted benzenesulfonylureas, for example, by hydrolysis or by adding on water.

(f) Benzenesulfonylureas of the formula Ia can be prepared from benzenesulfonyl halides of the formula VIII using $R^1$-substitutedureas or $R^1$-substituted bis(trialkylsilyl) ureas. The trialkylsilyl protective group can be removed from the resulting (trialkylsilyl)benzenesulfonylurea according to standard methods. Furthermore, the sulfonyl chlorides of the formula VIII can be reacted with parabanic acid to give benzenesulfonyl parabanic acids the hydrolysis of which, with mineral acids, affords the corresponding benzenesulfonylureas of the formula Ia.

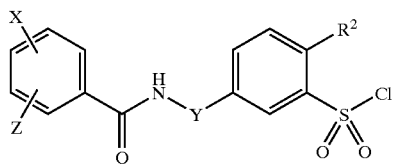

VIII (g) Benzenesulfonylureas of the formula Ia can be prepared by reacting amines of the formula $R^1$—$NH_2$ with benzenesulfonyl isocyanates of the formula IX. Likewise, amines of the formula $R^1$—$NH_2$ can be reacted with benzenesulfonylcarbamic acid esters, with -carbamoyl halides or with benzenesulfonylureas of the formula Ia in which $R^1$ is hydrogen to give compounds of the formula Ia.

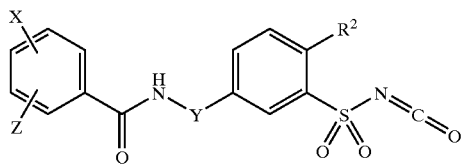

IX (h) Benzenesulfonylthioureas of the formula Ib can be prepared by reacting amines of the formula $R^1$—$NH_2$ with benzenesulfonyl isothiocyanates of the formula X.

Likewise, amines of the formula $R^1$—$NH_2$ can be reacted with benzenesulfonylcarbamic acid thioesters or -carbamoyl thiohalides to give compounds of the formula Ib.

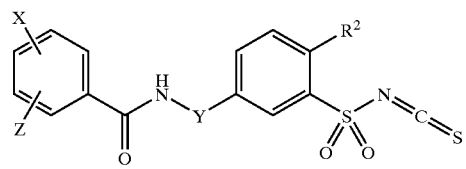

X (i) Appropriately substituted benzenesulfenyl- or -sulfinylureas can be oxidized with oxidizing agents such as hydrogen peroxide, sodium peroxide or nitrous acid to give benzenesulfonylureas of the formula Ia.

The starting materials for the abovementioned synthesis processes of the compounds of the formula I can be prepared by methods known per se, such as are described in the literature (for example in the standard works such as Houben-Weyl, Methoden der Organischen Chemie [Methods of Organic Chemistry], Georg Thieme Verlag, Stuttgart; Organic Reactions, John Wiley & Sons, Inc., New York; or in the abovementioned patent references), and under reaction conditions which are known and suitable for the reactions mentioned. Variants which are known per se but which are not mentioned in more detail here can also be utilized for these reactions. If desired, the starting materials can also be formed in situ, so that they are not isolated from the reaction mixture but are further reacted immediately.

Thus, appropriately substituted amines of the formula XI can be acylated and subjected to halosulfonation. In the formula XI, $R^2$ and Y have the meanings given above. Suitable acylating agents for acylating the amino group in the compounds of

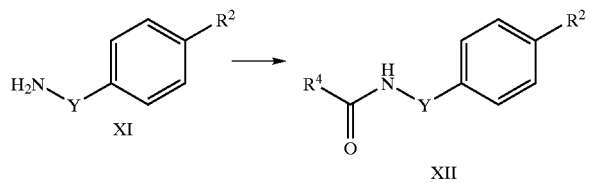

the formula XI are advantageously the alkyl esters, halides (for example chlorides or bromides) or anhydrides of carboxylic acids of the formula $R^4$—COB. $R^4$ is here, for example, a trihalomethyl residue, a $(C_1-C_4)$-alkyl residue or a phenyl residue. If $R^4$ is a phenyl residue, the compound of the formula $R^4$—COB is a benzoic acid derivative. The benzoic acid derivative can be unsubstituted or substituted by one or two identical or different residues X and Z. Here X and Z are as defined above, i. e. X can be hydrogen, $(C_1-C_6)$-alkyl or halogen and Z can be halogen, $(C_1-C_4)$-alkyl, $(C_1-C_4)$-alkoxy or nitro. The group B is a leaving group such as, for example, halogen, $(C_1-C_4)$-alkoxy, trihaloacetoxy or $(C_1-C_4)$-alkylcarbonyloxy. Examples of compounds of the formula $R^4$—COB are acetic anhydride, trihaloacetic anhydride, acetyl halides, trihaloacetyl halides, propionyl chloride, isobutyryl bromide and isobutyryl chloride, formic acid/acetic anhydride, benzoyl chloride and substituted benzoic acid derivatives, such as 5-chloro-2-methoxybenzoyl chloride or 5-chloro-2-methoxybenzoic anhydride or $(C_1-C_4)$-alkyl 5-chloro-2-methoxybenzoate, 5-tert-butyl-2-methoxybenzoyl chloride or 2,5-difluorobenzoyl chloride. The syntheses of the compounds of the formula XII are preferably carried out with addition of a tertiary amine base, such as, for example, pyridine or a trialkylamine, in the presence or absence of an inert solvent, the presence of a catalyst such as, for example, dimethylaminopyridine also being possible. The reaction is generally carried out at temperatures between approximately 0° C. and 160° C., preferably between 20° C. and 150° C. The acyl group in the compounds of the formula XII can be a protective group or, in the case of the benzoic acid derivatives, also part of the compounds of the formula I. Suitable inert solvents for the acylation are, for example, ethers, such as tetrahydrofuran, dioxane or glycol ethers, such as ethylene glycol monomethyl ether or ethylene glycol monoethyl ether (methylglycol or ethylglycol) or ethylene glycol dimethyl ether, ketones, such as acetone or butanone, nitriles, such as acetonitrile, nitro compounds, such as nitromethane, esters, such as ethyl acetate, amides, such as DMF or NMP, hexamethylphosphoric triamide, sulfoxides, such as DMSO, chlorinated hydrocarbons, such as dichloromethane, chloroform, trichloroethylene, 1,2-dichloroethane or carbon tetrachloride, or hydrocarbons, such as benzene, toluene or xylenes. Furthermore suitable are mixtures of these solvents with one another.

From the compounds of the formula XII, the sulfonamides of the formula XIII can be prepared according to methods known per se, under reaction conditions which are

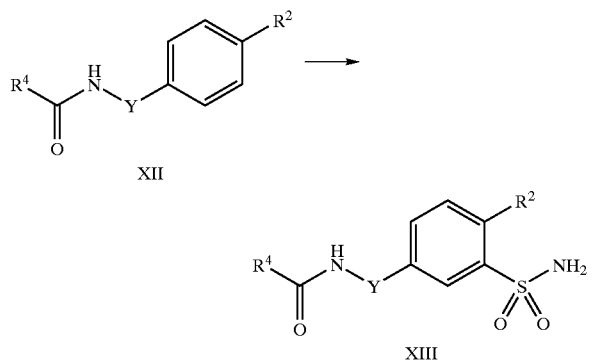

suitable and known for such reactions. Variants which are known per se but which are not mentioned in more detail here also can be utilized for these reactions. If desired, the syntheses can be carried out in one, two or several steps. Particular preference is given to processes in which the acylated amine of the formula XII is converted by electrophilic reagents in the presence or absence of inert solvents at temperatures between −10° C. and 120° C., preferably between 0° C. and 100° C., into aromatic sulfonic acids or their derivatives, such as, for example, sulfonyl halides. It is possible to carry out, for example, sulfonations using sulfuric acids or oleum, halosulfonations using halosulfonic acids, reactions with sulfuryl halides in the presence of anhydrous metal halides, or reactions with thionyl halides in the presence of anhydrous metal halides with subsequent oxidation, carried out in a manner known per se, to give aromatic sulfonyl chlorides. If the primary reaction products are sulfonic acids these can be converted into the sulfonyl halides either directly or by treatment with tertiary amines such as, for example, pyridine or trialkylamines or with alkali metal or alkaline earth metal hydroxides or reagents which form these basic compounds in situ, in a known manner using acid halides such as, for example, phosphorus trihalides, phosphorus pentahalides, phosphorus oxichlorides, thionyl halides or oxalyl halides. The conversion of the sulfonic acid derivatives into sulfonamides can be carried out in a manner known from the literature. Preference is given to reacting the sulfonyl chlorides in inert solvents at temperatures between 0° C. and 100° C. with aqueous ammonia in the absence or presence of an organic solvent. Furthermore, aromatic sulfonamides can be synthesized according to the processes described in the literature from the acylated amines of the formula XII by reaction with organo(alkali or alkaline earth) metallic reagents in inert solvents and under an atmosphere of inert gas at temperatures from −100° C. to 50° C., preferably from −100° C. to 30° C., and with sulfur dioxide and subsequent thermal treatment with amidosulfonic acid.

If the acyl group in the compound of the formula XIII acts as a protective group for the amino group, this protective group can be removed by treatment with acids or bases after the introduction of the sulfonamide group. Cleavage with aqueous acids or with acids in inert solvents may afford the acid addition salt of the amino compound. Suitable for this protective group removal are, for example, sulfuric acid, hydrohalic acids, such as hydrochloric acid or hydrobromic acid, phosphoric acids, such as orthophosphoric acid, or organic acids. The removal of the amino protective group in the compound of the formula XIII with bases can be carried out in aqueous or inert solvents. Suitable bases are, for example, alkali metal or alkaline earth metal hydroxides, such as sodium hydroxide, potassium hydroxide or calcium hydroxide, or alkali metal or alkaline earth metal alkoxides, such as sodium methoxide, sodium ethoxide, potassium methoxide or potassium ethoxide. From the sulfonamide-substituted amines or their acid addition compounds prepared in this manner, it is possible to prepare the benzenesulfonamides of the formula III by acylation with substituted benzoic acids or benzoic acid derivatives, as illustrated above for the acylation of the compounds of the formula XI.

The compounds of the formula I can have one or more chiral centers. Consequently, they can be obtained in their preparation as racemate or else, if optically active starting materials are used, in optically active form. If the compounds have two or more chiral centers, they can be obtained in the synthesis as mixtures of racemates from which the individual isomers can be isolated in pure form, for example by recrystallization from inert solvents. If desired, the racemates obtained can be separated by methods known per se, mechanically or chemically, into their enantiomers. Thus, diastereomers can be formed from the racemate by reaction with an optically active resolving agent. Suitable resolving agents for basic compounds are, for example, optically active acids, such as the R— or R,R— and S— or S,S-forms of tartaric acid, dibenzoyltartaric acid, diacetyltartaric acid, camphorsulfonic acids, mandelic acids, malic acid or lactic acid. For separation, it is furthermore possible to acylate carbinols with the aid of chiral acylating agents, for example R— or S-α-methylbenzyl isocyanate, followed by separation. The different forms of the diastereomers can be separated in a manner known per se, for example by fractional crystallization, and the enantiomers can be liberated from the diastereomersr in a manner known per se. Separation of enantiomers is furthermore possible by chromatography over optically active stationary phases.

Depending on the nature of the residues $R^1$, $R^2$, $R^3$, E, X, Y and Z, in individual cases one or other of the abovementioned processes for the preparation of the compounds of the formula I will be unsuitable, or at least require measures for the protection of active groups. Such cases, which are relatively rare, will easily be recognized by the person skilled in the art, and it does not cause any difficulties to employ another of the described synthetic routes successfully in such cases. With respect to the preparation of the compounds of the formula I to be used according to the invention, U.S. Pat. No. 5,574,069 (EP-A-612 724), U.S. Pat. No. 5,776,980, U.S. Pat. No. 5,698,596, and U.S. Pat. No. 5,652,268 (EP-A-727 416) are expressly incorporated herein by way of reference.

Owing to their ability to reduce or eliminate insufficient function of the vagal nervous system and thus vagal dysfunctions and/or a dysfunction of the autonomous nervous system, the compounds of the formula I are useful agents for the treatment and prophylaxis of diseases which are associated with such impaired functions or dysfunctions of the vagal nervous system or which are caused by them, or for the treatment or prophylaxis of which an increase or normalization of the activity of the vagal nervous system is aimed for. The effect of the compounds of the formula I on the vagal nervous system can be demonstrated, for example, in the pharmacological mouse model described below. The effect can also be demonstrated, for example, in rats, guinea pigs, rabbits, dogs, monkeys or pigs.

Diseases and pathological conditions where the treatment or prophylaxis of an impaired function of the vagal nervous system or a dysfunction of the autonomous nervous system is indicated have already been mentioned above. Besides being generally suitable for the treatment or prophylaxis of a dysfunction of the autonomous nervous system and in particular a vagal dysfunction, the compounds of the formula I and their physiologically acceptable salts are specifically suitable for use in disorders of the cardiovascular system and in heart diseases for the treatment or prophylaxis of a sympathovagal imbalance or for the treatment and prophylaxis of a vagal dysfunction of the heart. Examples of heart diseases and conditions of this kind are coronary heart disease, angina pectoris, cardiac infarction, postmyocardial infarction, cardiac insufficiency, cardiomyopathies, heart transplants, or vagal dysfunctions of the heart in cases of diabetes mellitus. Since the compounds of the formula I have, besides their known direct effect on the heart, i.e. besides the effect on the action potential of the heart muscle cells, also an indirect effect on the nervous system of the heart or on the parts of the nervous system which act on the heart, they can reduce or prevent undesirable consequences for the heart which are, in the state of disease in question, caused or mediated by the nervous system. Thus, it is possible to reduce or avoid further damage to the health, such as a weakening of the strength of the heart or sometimes fatal cardiac arrhythmias such as ventricular fibrillation. By eliminating or reducing the dysfunction of the autonomous nervous system, the compounds of the formula I and their physiologically acceptable salts lead to a normalization of the weakened strength of the heart and to the prevention of the development of cardiac arrhythmias which can lead to sudden cardiac death. Areas of use of the compounds of the formula I and/or their physiologically acceptable salts in the context of the present invention are therefore in particular also the use in cases of cardiac insufficiency and the prevention of cardiac arrhythmias such as fatal ventricular fibrillation and the prevention of sudden cardiac death. By selecting compounds of the formula I having a suitable activity profile with respect to the direct effect on the heart (=direct effect on the action potential of the heart muscle cells and accordingly direct effect on the contractile force and direct antiarrhythmic effect) on the one hand and the effect on the heart nerves on the other hand it is possible in a particularly efficient manner to influence heart diseases favorably with the aid of the compounds of the formula I. Depending on the particular symptoms, it may also be advantageous to employ compounds of the formula I which only have a relatively low direct effect on the heart and accordingly only have, for example, a relatively low direct effect on the contractile force of the heart or the generation of arrhythmias, but which can improve or normalize the strength of the heart or the heart rhythm by influencing the autonomous nervous system. As already mentioned, an impaired function of the vagal system and its consequences can also occur temporarily, for example in the case of oxygen deficiency of the heart. The compounds of the formula I are therefore also particularly suitable for use in angina pectoris or coronary heart disease where states of oxygen deficiency occur.

Furthermore, compounds of the formula I can generally be employed in cases of dysfunctions of the autonomous nervous system, in particular vagal dysfunction, which occur as a result of a metabolic disorder, such as, for example, diabetes mellitus.

The compounds of the formula I and their physiologically acceptable salts can therefore be used in animals, preferably mammals and in particular humans as a medicament per se, in mixtures with one another or together with other active compounds, in particular in the form of pharmaceutical preparations (or pharmaceutical compositions). A subject of the present invention thus is the use of the compounds of the formula I and/or their physiologically acceptable salts for preparing medicaments for the therapy or prophylaxis of the abovementioned syndromes. A subject of the invention also is the use of the compounds of the formula I and/or their physiologically acceptable salts for the therapy or prophylaxis of the abovementioned syndromes, and a subject of the invention are methods for the therapy or prophylaxis of the abovementioned syndromes in which an effective amount of one or more compounds of the formula I and/or their physiologically acceptable salts is administered to a human or animal patient in need thereof.

Medicaments utilizable according to the invention which comprise the compounds of the formula I and/or their physiologically acceptable salts can be administered enterally, for example orally or rectally, for example in the form of pills, tablets, coated tablets, sugar-coated tablets, granules, hard and soft gelatin capsules, suppositories, solutions, such as aqueous, alcoholic or oily solutions, juices, drops, syrups, emulsions or suspensions. The medicaments can also be administered parenterally, for example subcutaneously, intramuscularly or intravenously in the form of solutions for injection or solutions for infusion. Other suitable administration forms are, for example, percutaneous or topical application, for example in the form of ointments, creams, pastes, lotions, gels, sprays, powders, foams, aerosols or solutions, or the use in the form of implants.

The pharmaceutical preparations utilizable according to the invention can be prepared by known standard processes for preparing pharmaceutical preparations. To this end, one or more compounds of the formula I and/or their physiologically acceptable salts are mixed together with one or more solid or liquid pharmaceutical excipients and/or additives or auxiliaries and, if a combination preparation is desired, further pharmaceutically active compounds having therapeutic or prophylactic effect, and brought into a suitable administration form or dosage form which can then be used as a medicament in human medicine or veterinary medicine. The pharmaceutical preparations comprise a therapeutically or prophylactically effective dose of the compounds of the formula I and/or their physiologically acceptable salts, which normally is from 0.5 to 90% by weight of the pharmaceutical preparation. The amount of active compound of the formula I and/or its physiologically acceptable salts in the pharmaceutical preparations is generally from 0.2 mg to 1000 mg, preferably from 0.2 mg to 500 mg, particularly preferably from 1 mg to 500 mg, per unit but can also be higher, depending on the nature of the pharmaceutical preparation.

Suitable excipients are organic or inorganic substances which are suitable, for example, for enteral (for example oral) or parenteral (for example intravenous) administration or topical administrations and which do not react with the active compounds in an undesirable manner, for example water, vegetable oils, alcohols such as ethanol, isopropanol or benzyl alcohols, 1,2-propanediol, polyethylene glycols, glycerol triacetate, gelatin, carbohydrates, such as lactose or starch, magnesium stearate, talc, lanolin, petroleum jelly, acetonitrile, dimethylformamide, dimethylacetamide. It is also possible to employ mixtures of two or more excipients, for example mixtures of two or more solvents, in particular also mixtures of one or more organic solvents with water. As additives or auxiliaries, the pharmaceutical preparations can contain, for example, stabilizers, wetting agents, emulsifiers, solubilizers, thickeners, salts, for example for influencing the osmotic pressure, glidants, preservatives, colorants, flavorings, aromas and/or buffer substances. If desired, they can also comprise one or more further active compounds, for example one or more vitamins. It is also possible to lyophilize the compounds of the formula I and/or their physiologically acceptable salts, and to use the resulting lyophilisates for preparing preparations for injection, for example. Also suitable are liposomal preparations, in particular for topical administration.

The dosage of the active compound of the formula I to be administered and/or of a physiologically acceptable salt thereof when used according to the invention, depends on the individual case and has to be adapted to the individual circumstances to obtain an optimum effect, as is customary. It therefore depends on the nature and the seriousness of the disease to be treated, and also on the sex, the age, the weight and the individual responsiveness of the human or animal to be treated, on the effectiveness and the duration of action of the compounds used, on whether the treatment is an acute or chronic therapy or prophylaxis, or on whether other active compounds are administered in addition to compounds of the formula I. In general, a dosage range for the treatment of a dysfunction of the autonomous nervous system in humans of from approximately 0.1 mg to approximately 100 mg per kg and day, when administered to an adult of a weight of about 75 kg, is adequate for achieving the desired effect. Preference is given to a dosage range of from approximately 1 mg to approximately 10 mg per kg and day (in each case mg per kg of bodyweight). The daily dose can be administered as a single dose or be divided into more than one, for example two, three or four, individual doses. It can also be administered continuously. Depending on the individual behavior, it may be necessary to exceed or reduce the stated daily dose.

In addition to the effect on the autonomous nervous system, it has also been found that the compounds of the formula I have a synergistic effect with beta-receptor blockers which can advantageously be used in particular in the treatment and prophylaxis of heart diseases such as, for example, cardiac insufficiency. As is known, the use of beta-receptor blockers at low doses improves the symptoms in cases of cardiac insufficiency by depressing the sympathicus, whereas compounds of the formula I reestablish the disrupted balance between vagal and sympathetic nerves primarily via vagal stimulation. As demonstrated in the animal experiment described below, a combination of compounds of the formula I and beta-receptor blockers shows a superadditive or synergistic effect in the prevention of heart diseases or heart damage and is therefore particularly advantageously suitable, for example, for improving the symptoms in cases of cardiac insufficiency or for preventing or reducing cardiac arrhythmias, such as ventricular fibrillation, or for preventing sudden cardiac death. Expressed in a different way, the compounds of the formula I significantly improve the effect of beta-receptor blockers, for example on the heart. Thus, the compounds of the formula I are highly suitable for combinations with beta-receptor blockers.

A subject of the present invention therefore also is the treatment and prophylaxis of the abovementioned heart diseases such as, for example, cardiac insufficiency, angina pectoris, cardiac infarction, postmyocardial infarction or cardiac arrhythmias such as ventricular fibrillation, or the prevention of sudden cardiac death, and the treatment and prophylaxis of dysfunctions of the autonomous nervous system, in particular vagal dysfunction, specifically vagal dysfunction of the heart, by one or more compounds of the formula I and/or their physiologically acceptable salts in combination with one or more beta-receptor blockers and/or their physiologically acceptable salts. A subject of the invention also is the use of the compounds of the formula I and/or their physiologically acceptable salts for preparing medicaments for such a combination treatment or combination prophylaxis, and a subject are methods for such combination therapy or combination prophylaxis. A subject of the invention further are combinations of one or more compounds of the formula I and/or their physiologically acceptable salts and one or more beta-receptor blockers and/or their physiologically acceptable salts for the simultaneous, separate or sequential use in the conditions mentioned.

In the context of the combination treatment or combination prophylaxis according to the invention, the representatives of the two classes of active compounds can be administered in the form of a pharmaceutical preparation where both of them together are contained in the same pharmaceutical formulation unit, for example a tablet, i. e. in the form of a pharmaceutical combination preparation. But just so, they can be administered separately, for example in the form of pharmaceutical preparations each containing the representatives of only one of the two classes of the active compounds, where in this case the representatives of the two classes of active compounds can be administered simultaneously, directly one after the other or sequentially including, for example, after a relatively large interval. All these types are embraced by the present invention. Depending on the circumstances of the individual case, it may be more favorable to administer the representatives of the two classes of active compounds in the form of a pharmaceutical combination preparation in which they are present together in a fixed ratio in the same pharmaceutical formulation, or to administer them separately in the form of more than one, for example two, individual pharmaceutical preparations in each of which, for example, only a single active compound is contained. In the latter case, the individual pharmaceutical preparations, then forming a kit of parts, can in suitable primary packaging be present together in a common external packaging, if desired together with instructions for use referring to the combination use according to the invention, or the individual pharmaceutical preparations can be present in separate external packagings, if desired in each case together with instructions for use referring to the combination use according to the invention. All such products and forms of presentation suitable for the use according to the invention are embraced by the present invention.

A subject of the present invention accordingly also are products or articles, comprising one or more compounds of the formula I

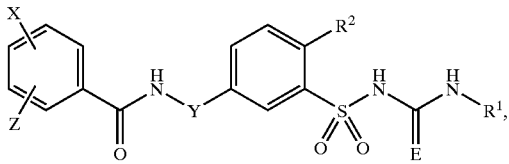

in which

R¹ is hydrogen, methyl or trifluoromethyl;
R² is hydrogen, halogen, $(C_1-C_6)$-alkyl, $(C_1-C_6)$-alkoxy, $(C_1-C_6)$-alkoxy-$(C_1-C_4)$-alkoxy-, $(C_1-C_6)$-alkoxy-$(C_1-C_4)$-alkoxy-$(C_1-C_4)$-alkoxy-, $(C_1-C_6)$-alkylthio, $(C_1-C_6)$-fluoroalkoxy or $(C_1-C_6)$-fluoroalkyl;
E is oxygen or sulfur;
Y is a hydrocarbon residue of the formula —$(CR^3{}_2)_n$— in which the residues R³ independently of one another are each hydrogen or $(C_1-C_2$-alkyl and n is 1, 2, 3 or 4;
X is hydrogen, halogen or $(C_1-C_6)$-alkyl;
Z is halogen, nitro, $(C_1-C_4)$-alkoxy or $(C_1-C_4)$-alkyl;

in all their stereoisomeric forms and mixtures thereof in all ratios, and/or their physiologically acceptable salts, in combination or as combination preparation with one or more beta-receptor blockers and/or their physiologically acceptable salts, for simultaneous, separate or sequential use in the treatment or prophylaxis of dysfunctions of the autonomous nervous system, a vagal dysfunction, a vagal dysfunction of the heart or in the treatment or prophylaxis of the above-mentioned diseases, in particular heart diseases such as, for example, cardiac insufficiency, angina pectoris, cardiac infarction, postmyocardial infarction or cardiac arrhythmias such as ventricular fibrillation, or in the prevention of sudden cardiac death.

A subject of the present invention in particular are the pharmaceutical combination preparations mentioned in which the representatives of the two classes of active compounds are present together in the same pharmaceutical formulation, i.e. pharmaceutical preparations which comprise one or more compounds of the formula I

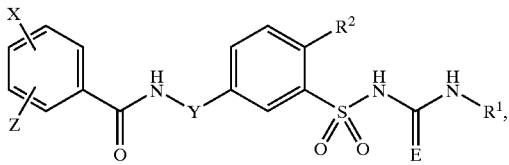

in which

R¹ is hydrogen, methyl or trifluoromethyl;
R² is hydrogen, halogen, $(C_1-C_6)$-alkyl, $(C_1-C_6)$-alkoxy, $(C_1-C6)$-alkoxy-$(C_1-C_4)$-alkoxy-, $(C_1-C_6)$-alkoxy-$(C_1-C_4)$-alkoxy-$(C_1-C_4)$-alkoxy-, $(C_1-C_6)$-alkylthio, $(C_1-C_6)$-fluoroalkoxy or $(C_1-C_6)$-fluoroalkyl;
E is oxygen or sulfur;
Y is a hydrocarbon residue of the formula —$(CR^3{}_2)_n$— in which the residues R³ independently of one another are each hydrogen or $(C_1-C_2$-alkyl and n is 1, 2, 3 or 4;

X is hydrogen, halogen or $(C_1-C_6)$-alkyl;
Z is halogen, nitro, $(C_1-C_4)$-alkoxy or $(C_1-C_4)$-alkyl;
in all their stereoisomeric forms and mixtures thereof in all ratios, and/or their physiologically acceptable salts, one or more beta-receptor blockers and/or their physiologically acceptable salts and a physiologically acceptable carrier, i.e. one or more physiologically acceptable excipients and/or additives or auxiliaries.

All the above illustrations, for example with respect to excipients, auxiliaries or additives, to pharmaceutical forms such as tablets, sugar-coated tablets, capsules or solutions, and their preparation, to possible administration forms, such as oral or intravenous administration, to the use in human medicine and veterinary medicine, or to the diseases which can be treated, etc., apply, correspondingly, to the products and pharmaceutical preparations described above. In this context, the beta-receptor blockers are to be considered as being an example of the further pharmaceutically active compounds which, in addition to the compounds of the formula I, may be present in the pharmaceutical preparations mentioned further above. All the illustrations given further above for the compounds of the formula I themselves also apply, correspondingly, to the compounds of the formula I contained in the products and the pharmaceutical preparations, for example the illustrations with respect to the individual residues and groups, to the preferred compounds of the formula I or to their salts. In pharmaceutical preparations containing compounds of the formula I together with beta-receptor blockers in the same pharmaceutical formulation also salts may be present which are formed by the compounds of these classes with one another, i. e. salts which contain the beta-receptor blocker (or the beta-receptor blockers), which are organic amino compounds, in protonated form as cation and the compound (or the compounds) of the formula I in deprotonated form as anion. The ratio by weight of the compounds of the formula I to the beta-receptor blockers in the pharmaceutical preparations in which both active compounds are present in the same pharmaceutical formulation is generally from 500 to 0.02, preferably from 100 to 0.1, parts by weight of the compound (or the compounds) of the formula I per part by weight of the beta-receptor blocker (or the beta-receptor blockers). For example, the ratio by weight can be about 35 parts by weight of the compound of the formula I per part by weight of the beta-receptor blocker, or it can about 1 part by weight of the compound of the formula I per part by weight of the beta-receptor blocker As compounds of the formula I, both the pharmaceutical preparations to be used according to the invention which do not contain any beta-receptor blockers and the products and the pharmaceutical preparations according to the invention which do contain beta-receptor blockers preferably comprise one or more of the compounds selected from the group consisting of 1-[[5-[2-(5-chloro-2-methoxybenzamido)ethyl]-2-methoxyphenyl]sulfonyl]-3-methylthiourea, 1-[[5-[2-(5-chloro-2-methoxybenzamido)ethyl]-2-(2-methoxyethoxy)phenyl]sulfonyl]-3-methylthiourea and 1-[[5-[2-(5-tert-butyl-2-methoxybenzamido)ethyl]-2-methoxyphenyl]sulfonyl]-3-methylthiourea and/or their physiologically acceptable salts, preferred salts of these compounds being the sodium salts.

Suitable beta-receptor blockers for the combination treatment and combination prophylaxis according to the invention and for the products and pharmaceutical preparations according to the invention are, for example, the following compounds: alprenolol, oxprenolol, penbutolol, bupranolol, metoprolol, betaxolol, atenolol, acebutolol, metipranolol, propranolol, nadolol, pindolol, timolol, sotalol, carvedilol, bisoprolol, celiprolol, carazolol, talinolol, mepindolol, carteolol, tertatolol, bopindolol. Preferred beta-receptor blockers are propanolol, atenolol, bisoprolol and carvedilol.

When combining compounds of the formula I with beta-receptor blockers, in general lower dosages of the compounds of the formula I and/or the beta-receptor blockers are required to achieve the desired effect than when the compounds of only one class of active compounds are used. A preferred dosage of the compounds of the formula I in combination with a beta-receptor blocker is in the range from approximately 0.3 mg to approximately 15 mg, preferably from approximately 1 mg to approximately 10 mg, per kg of bodyweight and day. The dosage of the beta-receptor blockers in the combination depends on the dosage customary for the individual compound in question. Preference is given to using the lowest customary dosage for the substance in question and the area of use in question. The above illustrations with respect to the dosage of the compounds of the formula I as individual active compounds apply, correspondingly, to the combination use according to the invention, for example with respect to the necessary adaptation of the dosage to the circumstances of the individual case or to a division of the dose into individual doses.

Owing to their effect on the autonomous nervous system, the compounds of the formula I and their salts can be used not only as pharmaceutically active compounds in human medicine and veterinary medicine but also as a scientific tool or as an auxiliary for biochemical investigations in which such an effect is intended, and also for diagnostic purposes, for example in the in vitro diagnosis of cell samples or tissue samples.

The present invention also provides the compounds of the formula I per se which have hitherto not been described, and their physiologically acceptable salts. In particular, the invention provides the novel substances per se described in the working examples, for example 1-[[5-[2-(5-tert-butyl-2-methoxybenzamido)ethyl]-2-methoxyphenyl]sulfonyl]-3-methylthiourea and its physiologically acceptable salts including its sodium salt, the use of the novel compounds as pharmaceutically active compounds, and pharmaceutical preparations which comprise one or more of these compounds and a physiologically acceptable carrier, i.e. one or more physiologically acceptable excipients and/or additives or auxiliaries. The above illustrations apply correspondingly to these pharmaceutical preparations, excipients and auxiliaries.

Besides the compounds described in the working examples, for example also the compounds of the formula I compiled below can be used according to the invention.

(1) 1-[[5-[2-(5-tert-butyl-2-methoxybenzamido)propyl]-2-methoxyphenyl]sulfonyl]-3-methylthiourea (2) 1-[[5-[2-(5-tert-butyl-2-methoxybenzamido)butyl]-2-methoxyphenyl]sulfonyl]-3-methylthiourea (3) 1-[[5-[2-(5-tert-butyl-2-methoxybenzamido)ethyl]-2-ethoxyphenyl]sulfonyl]-3-methylthiourea (4) 1-[[5-[2-(5-tert-butyl-2-methoxybenzamido)ethyl]-2-propoxyphenyl]sulfonyl]-3-methylthiourea (5) 1-[[5-[2-(5-tert-butyl-2-methoxybenzamido)ethyl]-2-ethylphenyl]sulfonyl]-3-methylthiourea (6) 1-[[5-[2-(5-tert-butyl-2-methoxybenzamidoethyl]-2-methylphenyl]sulfonyl]-3-methylthiourea (7) 1-[[5-[2-(5-tert-butyl-2-methoxybenzamido)ethyl]-2-isopropylphenyl]sulfonyl]-methylthiourea (8) 1-[[5-[2-(5-tert-butyl-2-methoxybenzamido)ethyl]-2-bromophenyl]sulfonyl]-3-methylthiourea (9) 1-[[5-[2-(5-tert-butyl-2-methoxybenzamido)ethyl]-2-fluorophenyl]sulfonyl]-3-methylthiourea

(10) 1-[[5-[2-(5-tert-butyl-2-methoxybenzamido)ethyl]-2-trifluoromethoxyphenyl]sulfonyl]-3-methylthiourea

(11) 1-[[5-[2-(5-tert-butyl-2-methoxybenzamido)ethyl]-2-methylthiophenyl]sulfonyl]-3-methylthiourea

(12) 1-[[5-[2-(5-tert-butyl-2-methoxybenzamido)ethyl]-2-ethylthiophenyl]sulfonyl]-3-methylthiourea

(13) 1--[[5-[2-(5-tert-butyl-2-methoxybenzamido)ethyl]-2-ispropoxyphenyl]sulfonyl]-3-methylthiourea

(14) 1-[[5-[(5-tert-butyl-2-methoxybenzamido)methyl]-2-methoxyphenyl]sulfonyl]-3-methylthiourea

(15) 1-[[5-[2-(5-(1,1-dimethylpropyl)-2-methoxybenzamido)ethyl]-2-methoxyphenyl]sulfonyl]-3-methylthiourea

(16) 1-[[5-[2-(5-sec-butyl-2-methoxybenzamido)ethyl]-2-methoxyphenyl]sulfonyl]-3-methylthiourea

(17) 1-[[5-[2-(5-n-butyl-2-methoxybenzamido)ethyl]-2-methoxyphenyl]sulfonyl]-3-methylthiourea

(18) 1-[[5-[2-(5-tert-butyl-2-methoxybenzamido)propyl]-2-methoxyphenyl]sulfonyl]-3-methylurea

(19) 1-[[5-[2-(5-tert-butyl-2-methoxybenzamido)butyl]-2-methoxyphenyl]sulfonyl]-3-methylurea

(20) 1-[[5-[2-(5-tert-butyl-2-methoxybenzamido)ethyl]-2-ethoxyphenyl]sulfonyl]-3-methylurea

(21) 1-[[5-[2-(5-tert-butyl-2-methoxybenzamido)ethyl]-2-propoxyphenyl]sulfonyl]-3-methylurea

(22) 1-[[5-[2-(5-tert-butyl-2-methoxybenzamido)ethyl]-2-ethylphenyl]sulfonyl]-3-methylurea

(23) 1-[[5-[2-(5-tert-butyl-2-methoxybenzamido)ethyl]-2-methylphenyl]sulfonyl]-3-methylurea

(24) 1-[[5-[2-(5-tert-butyl-2-methoxybenzamido)ethyl]-2-isopropylphenyl]sulfonyl]-3-methylurea

(25) 1-[[5-[2-(5-tert-butyl-2-methoxybenzamido)ethyl]-2-bromophenyl]sulfonyl]-3-methylurea

(26) 1-[[5-[2-(5-tert-butyl-2-methoxybenzamido)ethyl]-2-fluorophenyl]sulfonyl]-3-methylurea

(27) 1-[[5-[2-(5-tert-butyl-2-methoxybenzamido)ethyl]-2-trifluoromethoxyphenyl]sulfonyl]-3-methylurea

(28) 1-[[5-[2-(5-tert-butyl-2-methoxybenzamido)ethyl]-2-methylthiophenyl]sulfonyl]-3-methylurea

(29) 1-[[5-[2-(5-tert-butyl-2-methoxybenzamido)ethyl]-2-ethylthiophenyl]sulfonyl]-3-methylurea

(30) 1-[[5-[2-(5-tert-butyl-2-methoxybenzamido)ethyl]-2-isopropoxyphenyl]sulfonyl]-3-methylurea

(31) 1-[[5-[(5-tert-butyl-2-methoxybenzamido)methyl]-2-methoxyphenyl]sulfonyl]-3-methylurea

(32) 1-[[5-[2-(5-(1,1-dimethylpropyl)-2-methoxybenzamido)ethyl]-2-methoxyphenyl]sulfonyl]-3-methylurea

(33) 1-[[5-[2-(5-sec-butyl-2-methoxybenzamido)ethyl]-2-methoxyphenyl]sulfonyl]-3-methylurea

(34) 1-[[5-[2-(5-n-butyl-2-methoxybenzamido)ethyl]-2-methoxyphenyl]sulfonyl]-3-methylurea

(35) 1-[[5-[2-(5-isopropyl-2-methoxybenzamido)ethyl]-2-methoxyphenyl]sulfonyl]-3-methylurea

EXAMPLES

Example 1

1-[[5-[2-(5-tert-Butyl-2-methoxybenzamido)ethyl]-2-methoxyphenyl]sulfonyl]-3-methylthiourea

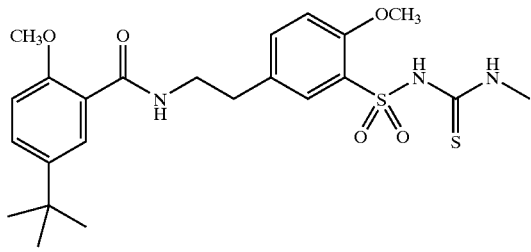

0.286 g (0.68 mmol) of 5-[2-(5-tert-butyl-2-methoxybenzamido)ethyl]-2-methoxybenzenesulfonamide were dissolved in 7.5 ml of dimethylformamide and, after addition of 0.1 g of potassium carbonate, admixed with 0.68 ml of a 1 M solution of methyl isothiocyanate in dimethylformamide and stirred at 80° C. for 2 hours. The cooled reaction mixture was poured into dilute aqueous hydrochloric acid, and the precipitate was filtered off with suction and dried in the air. The product had a melting point of 201–203° C.

Preparation of the Starting Material 1.51 g (10.0 mmol) of 2-(4-methoxyphenyl)ethylamine were dissolved in 40 ml of pyridine and admixed with a spatula tip of 4-dimethylaminopyridine and then with a solution of 2.15 g (10.5 mmol) of 5-tert-butyl-2-methoxybenzoyl chloride. After the 2-(4-methoxyphenyl) ethylamine had been converted completely, the reaction mixture was poured into cold dilute hydrochloric acid, and the precipitated product was filtered off with suction and dried to give 5-tert-butyl-2-methoxy-N-[2-(4-methoxyphenyl)ethyl]benzamide as a colorless solid. The benzamide was introduced into cold chlorosulfonic acid. After the benzamide had been converted completely, the reaction mixture was poured onto ice and filtered off with suction, and the precipitate was dissolved in acetone. This solution was admixed with excess concentrated aqueous ammonia. After the exothermic reaction had subsided, the mixture was concentrated to a third of its original volume and the precipitate was filtered off with suction. The 5-[2-(5-tert-butyl-2-methoxybenzamido)ethyl]-2-methoxybenzenesulfonamide was obtained in the form of colorless crystals of melting point 165–168° C.

Example 2

1-[[5-[2-(5-tert-Butyl-2-methoxybenzamido)ethyl]-2-methoxyphenyl]sulfonyl]-3-methylurea

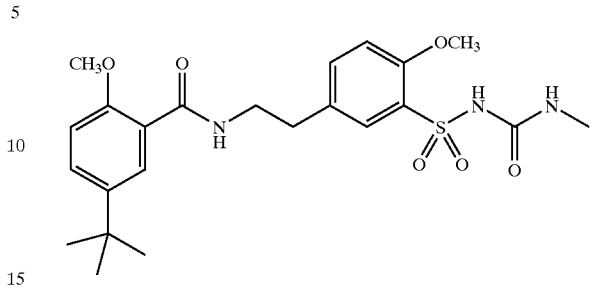

0.252 g (0.5 mmol) of 1-[[5-[2-(5-tert-butyl-2-methoxybenzamido)ethyl]-2-methoxyphenyl]sulfonyl]-3-methylthiourea (Example 1) were dissolved in 2.5 ml of 2 N aqueous sodium hydroxide solution and admixed with ice-cooling with 0.25 ml of 30% strength hydrogen peroxide. The solution was stirred at room temperature for 24 h and poured into a mixture of ice-water and 2 N hydrochloric acid. Drying in the air gave white crystals of melting point 209–212° C.

Example 3

1-[[5-[2-(5-lsopropyl-2-methoxybenzamido)ethyl]-2-methoxyphenyl]sulfonyl]-3-methylthiourea

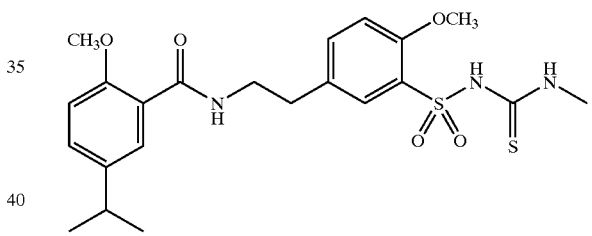

The preparation was carried out analogously to Example 1. White crystals of melting point 177–179° C. were obtained.

Example 4

1-[[5-[2-(5 Chloro-2-methoxybenzamido)ethyl]-2-methoxyphenyl]sulfonyl]-3-methylthiourea

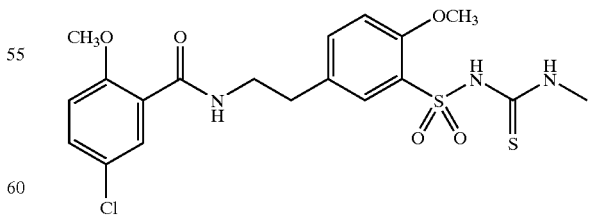

The preparation of this substance is described in U.S. Pat. No. 5,574,069 (EP-A-612 724) which is incorporated herein by reference and the contents of which regarding the preparation of the substance are part of the present disclosure.

Example 5

1-[[5-[2-(5-Chloro-2-methoxybenzamido)ethyl]-2-(2-methoxyethoxy)phenyl]sulfonyl]-3-methylthiourea

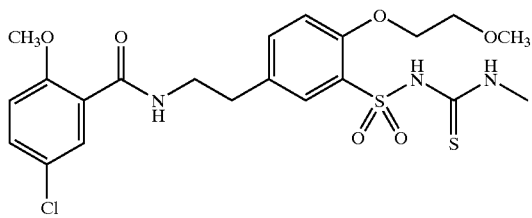

The preparation of this substance is described in U.S. Pat. No. 5,652,268 (EP-A-727 416) which is incorporated herein by reference and the contents of which regarding the preparation of the substance are part of the present disclosure.

Example 6

1-[[5-[2-(5-tert-Butyl-2-methoxybenzamido)ethyl]-2-(2-methoxyethoxy)phenyl]sulfonyl]-3-methylthiourea

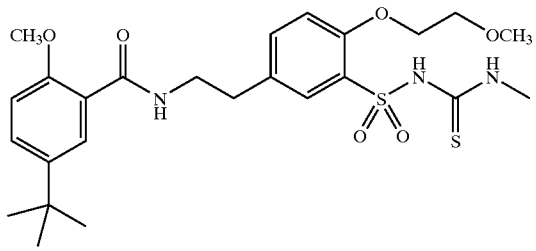

The preparation was carried out analogously to Example 1 using 5-[2-(5-tert-butyl-2-methoxybenzamido)ethyl]-2-(2-methoxyethoxy)benzenesulfonamide. Instead of potassium carbonate, sodium hydride was used as base in the reaction with methyl isothiocyanate analogously to Example 5. The product had a melting point of 61° C.

Example 7

1-[[5-[2-(5-tert-Butyl-2-methoxybenzamido)ethyl]-2-methoxyphenyl]sulfonyl]m-3-methylthiourea Sodium Salt

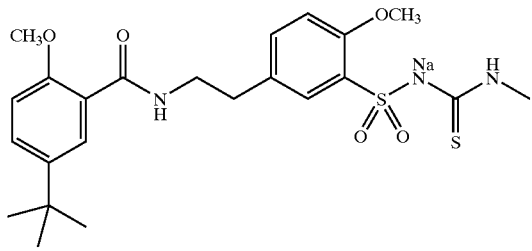

4.93 g of 1-[[5-[2-(5-tert-butyl-2-methoxybenzamido)ethyl]-2-methoxyphenyl]sulfonyl]-3-methylthiourea (Example 1) were introduced into 32 ml of methanol in which 0.425 g of solid sodium hydroxide had been dissolved before. After 15 min of stirring, 125 ml of methyl tert-butyl ether were added to the clear solution. With stirring, the sodium salt was allowed to crystallize out and then filtered off with suction, washed with a little cold methyl tert-butyl ether and dried. Yield 5.09 g. Melting point: 235–250° C. (decomposition). IR spectrum (Nujol): 1646.1 cm$^{-1}$.

EXAMPLES OF PHARMACEUTICAL PREPARATIONS

Example A

Tablet

To prepare tablets, 1-[[5-[2-(5-chloro-2-methoxybenzamido)ethyl]-2-methoxyphenyl]sulfonyl]-3-methylthiourea (Example 4), low-substituted hydroxypropylcellulose (L-HPC), polyvinylpyrrolidone (Povidone 25) and croscarmellose sodium (crosslinked sodium carboxymethylcellulose) were granulated moistened with water. The granules were passed through a 1–1.5 mm sieve, mixed with croscarmellose sodium and magnesium stearate and compacted to tablets. Amounts per tablet:

| | |
|---|---|
| Compound of Example 4 | 600 mg |
| L-HPC | 95 mg |
| Povidone 25 | 15 mg |
| Croscarmellose sodium | 60 mg |
| Magnesium stearate | 20 mg |

Example B

Aqueous Solution for Intravenous Administration

To prepare 10 ml of solution comprising 10 mg of active compound per ml, 100 mg of the sodium salt of 1-[[5-[2-(5-chloro-2-methoxybenzamido)ethyl]-2-methoxyphenyl]sulfonyl]-3-methylthiourea (see Example 4) were dissolved in 10 ml of isotonic (0.9% strength) sodium chloride solution.

Pharmacological Investigations

1. Effect on Vagal Dysfunction

The substances were investigated using the model of chloroform-induced ventricular fibrillation in the mouse (see J. W. Lawson, Antiarrhythmic activity of some isoquinoline derivatives determined by a rapid screening procedure in the mouse; J. Pharmacol. Exp. Ther. 1968, 160, 22–31). The test substance was dissolved in a mixture of dimethyl sulfoxide (DMSO) and 10% strength sodium bicarbonate solution and administered intraperitoneally (i.p.). After 30 minutes, the mouse was anesthetized with chloroform in a beaker. As soon as, in deep anesthesia, respiratory arrest had occurred (toxic anesthesia stage), the thorax of the animal was opened using a pair of scissors and the heartbeat was inspected visually. Here, it is possible to determine on first sight whether the heart is beating, fibrillating or arrested. The respiratory arrest triggered by chloroform leads, via absolute anoxia (lack of oxygen) in combination with a direct stimulating effect of chloroform on the sympathetic nervous system, to a potent stimulation of the sympathicus, which in turn in combination with the energy deficit in the heart caused by lack of oxygen results in fatal arrhythmia, i.e. ventricular fibrillation. This toxic chloroform anesthesia led to ventricular fibrillation in 100% of the untreated mice (control). The percentage of the mice with ventricular fibrillation in the individual test groups is shown in Table 1.

TABLE 1

Chloroform-induced ventricular fibrillation in the mouse

| | Proportion of fibrillation (in %) | |
|---|---|---|
| Substance (dose) | without atropine | with atropine (1 mg/kg i.v.) |
| untreated control | 100% | 100% |
| Example 1 (3 mg/kg i.p.) | 30%# | 90%* |
| Example 2 (1 mg/kg i.p.) | 60%# | 100%* |
| Example 3 (3 mg/kg i.p.) | 60%# | |
| 1-[[5-[2-(5-chloro-2-methoxybenzamido)ethyl]-2-methoxyphenyl]sulfonyl]-3-methylthiourea sodium salt (see Example 4) (10 mg/kg i.p.) | 50%# | 90%* |
| Example 5 (10 mg/kg i.p.) | 60%# | 100%* |
| carbachol (60 μg/kg i.v.) | 60%# | 100%* |
| physostigmine (1 mg/kg s.c.) | 70%# | 100%* | significant inhibition of ventricular fibrillation by the substances (n = 10) compared to control animals (n = 300), p < 0.005
*significant reduction of the protective effect of the substances by atropine (n = 10), p < 0.05

The results show that the compounds of the formula I significantly reduce the occurrence of ventricular fibrillation. The observed influence of atropine, the classic blocker of muscarinic (vagal) receptors of the autonomous nervous system, which blocks the effect of the vagal transmitter acetylcholine on the receptor level, gives an indication of the mechanism of action. Atropine reduces or prevents the protective effect of the compounds of the formula I. This neutralization of the protective effect of the substances by atropine points unambiguously to a vagal mechanism of action. A similar protective effect could be generated by vagal stimulation with carbachol, a more stable analog of the natural vagal transmitter acetylcholine, where the protective effect could likewise be inhibited by atropine. Furthermore, the cholinesterase inhibitor physostigmine, which slows down the degradation of acetylcholine, mimicked the protective effect of the compounds of the formula I, an effect which was likewise neutralized by atropine.

2. Effect of Combinations of Compounds of the Formula I with Beta-receptor Blockers In the same animal model as in the experiment "effect on vagal dysfunction" described above, it was demonstrated that a combined treatment with beta-receptor blockers and compounds of the formula I results in a favorable synergistic effect. The active compounds were administered i.v. (intravenously) or i.p. (intraperitoneally). In one experiment, 10 mg/kg of 1-[[5-[2-(5-chloro-2-methoxybenzamido) ethyl]-2-methoxyphenyl]sulfonyl]-3-methylthiourea sodium salt (see Example 4; dissolved in DMSO/10% strength sodium bicarbonate solution) were combined with 0.3 mg/kg of propanolol (dissolved in distilled water), a standard beta-blocker. It was found that the combined pretreatment of the animals with the two substances had a synergistic effect. The proportion of fibrillation could be lowered further than with the individual substances, in a statistically significant manner. For comparison, a 10 times higher dose of 3 mg/kg of propanolol was used. It was found that 0.3 mg/kg of propanolol in combination with 10 mg/kg of 1-[[5-[2-(5-chloro-2-methoxybenzamido)ethyl]-2-methoxyphenyl]sulfonyl]-3-methylthiourea sodium salt gave approximately the same result as 3 mg/kg of propranolol, or was even superior to the effect of a propanolol dose of 3 mg/kg. In another experiment, 3 mg/kg of 1-[[5-[2-(5-tert-butyl-2-methoxybenzamido)ethyl]-2-methoxyphenyl]sulfonyl]-3-methylthiourea (Example 1) and 3 mg/kg of atenolol were combined in an analogous manner. The results of the combination treatments are shown in Table 2.

TABLE 2

Synergistic effect of compounds of the formula I and beta-receptor blockers

| Substance (Dose) | Proportion of fibrillation in % |
|---|---|
| untreated control (n = 100) | 100% |
| 1-[[5-[2-(5-chloro-2-methoxybenzamido)ethyl]-2-methoxyphenyl]sulfonyl]-3-methylthiourea sodium salt (see Example 4) (10 mg/kg i.v.) | 50%* |
| propranolol (0.3 mg/kg i.v.) | 37%* |
| propranolol (3 mg/kg i.v.) | 17%* |
| 1-[[5-[2-(5-chloro-2-methoxybenzamido)ethyl]-2-methoxyphenyl]sulfonyl]-3-methylthiourea sodium salt (10 mg/kg i.v.) plus propranolol (0.3 mg/kg i.v.) | 10%*# |
| 1-[[5-[2-(5-tert-butyl-2-methoxybenzamido)ethyl]-2-methoxyphenyl]sulfonyl]-3-methylthiourea (Example 1) (3 mg/kg i.p.) | 53%* |
| atenolol (3 mg/kg i.v.) | 48%* |
| 1-[[5-[2-(5-tert-butyl-2-methoxybenzamido)ethyl]-2-methoxyphenyl]sulfonyl]-3-methylthiourea (3 mg/kg i.p.) plus atenolol (3 mg/kg i.v.) | 25%*# |

*p < 0.001 vs. untreated control; #p < 0.05 vs. beta-receptor blocker or compound of the formula I; n = 30 for all treated groups.

We claim:

1. A method for the treatment or prophylaxis of a disfunction of the autonomous nervous system, which comprises administering to a host in need of such treatment or prophylaxis an effective amount of a benzenesulfonyl(thio) urea of the formula I or a physiologically acceptable salt thereof,

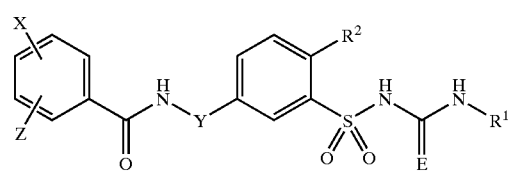

in any stereoisomeric form, or a mixture of benzenesulfonyl(thio)ureas of the formula I or physiologically acceptable salts thereof, in any stereoisomeric forms, in which $R^1$ is hydrogen, methyl or trifluoromethyl;

$R^2$ is hydrogen, halogen, $(C_1-C_6)$-alkyl, $(C_1-C_6)$-alkoxy, $(C_1-C_6)$-alkoxy-$(C_1-C_4)$-alkoxy-, $(C_1-C_6)$-alkoxy-$(C_1-C_4)$-alkoxy-$(C_1-C_4)$-alkoxy-, $(C_1-C_6)$-alkylthio, $(C_1-C_6$-fluoroalkoxy or $(C_1-C_6)$-fluoroalkyl;

E is oxygen or sulfur;

Y is a hydrocarbon residue of the formula —$(CR^3_2)_n$— in which the residues $R^3$ independently of one another are each hydrogen or $(C_1-C_2)$-alkyl and n is 1, 2, 3 or 4;

X is hydrogen, halogen or $(C_1-C_6)$-alkyl;

Z is halogen, nitro, $(C_1-C_4)$-alkoxy or $(C_1-C_4)$-alkyl, and which further comprises the simultaneous, separate or sequential administration to the host of at least one beta-receptor blocker or a physiologically acceptable salt thereof.

2. A method as claimed in claim 1, wherein in the formula I

R² is hydrogen, halogen, $(C_1–C_6)$-alkyl, $(C_1–C_6)$-alkoxy, $(C_1–C_4)$-alkoxy-$(C_1–C_4)$-alkoxy-, $(C_1–C_4)$-alkoxy-$(C_1–C_4)$-alkoxy-$(C_1–C_4)$-alkoxy-, $(C_1–C_6)$-alkylthio, $(C_1–C_6)$-fluoroalkoxy or $(C_1–C_6)$-fluoroalkyl;

X is halogen or $(C_3–C_6)$-alkyl.

3. A method as claimed in claim 1, wherein in the formula I

R¹ is hydrogen or methyl;

R² is hydrogen, halogen, $(C_1–C_6)$-alkyl, $(C_1–C_6)$-alkoxy, $(C_1–C_4)$-alkoxy-$(C_1–C_4)$-alkoxy-, $(C_1–C_4)$-alkoxy-$(C_1–C_4)$-alkoxy-$(C_1–C_4)$-alkoxy-, $(C_1–C_6)$-alkylthio, $(C_1–C_6)$-fluoroalkoxy or $(C_1–C_6)$-fluoroalkyl;

Y is a hydrocarbon residue of the formula —$(CR^3_2)_n$— in which the residues $R^3$ independently of one another are each hydrogen or methyl and n is 1, 2, 3 or 4;

X is halogen or $(C_3–C_6)$-alkyl;

Z is $(C_1–C_4)$-alkoxy.

4. A method as claimed in claim 1, wherein in the formula I

R¹ is hydrogen or methyl;

R² is $(C_1–C6)$-alkyl, $(C_1–C_6)$-alkoxy, $(C_1–C_4)$-alkoxy-$(C_1–C_4)$-alkoxy- or $(C_1–C_4)$-alkoxy-$(C_1–C_4)$-alkoxy-$(C_1–C_4)$-alkoxy-;

Y is a hydrocarbon residue of the formula —$(CR^3_2)_n$— in which the residues $R^3$ independently of one another are each hydrogen or methyl and n is 1, 2, 3 or 4;

X is halogen or $(C_3–C_6)$-alkyl;

Z is $(C_1–C_4)$-alkoxy.

5. A method as claimed in claim 1, wherein in the formula I

R¹ is hydrogen or methyl;

R² is methyl, methoxy or 2-methoxyethoxy-;

Y is a hydrocarbon residue of the formula —$(CR^3_2)_n$— in which the residues $R^3$ independently of one another are each hydrogen or methyl and n is 2 or 3;

X is halogen or $(C_3–C_6)$-alkyl;

Z is $(C_1–C_4)$-alkoxy.

6. A method as claimed in claim 1, wherein in the formula I

R¹ is methyl;

R² is methyl, methoxy or 2-methoxyethoxy-;

E is sulfur;

Y is a hydrocarbon residue of the formula —$(CH_2)_n$— in which n is 2 or 3;

X is halogen or $(C_3–C_6)$-alkyl;

Z is $(C_1–C_4)$-alkoxy.

7. A method as claimed in claim 1, which comprises administering 1-[[5-[2-(5-chloro-2-methoxybenzamido)ethyl]-2-methoxyphenyl]sulfonyl]-3-methylthiourea, 1-[[5-[2(5-chloro-2-methoxybenzamido)ethyl]-2-(2-methoxyethoxy)phenyl]sulfonyl]-3-methylthiourea, or 1-[[5-[2-(5-tert-butyl-2-methoxybenzamido)ethyl]-2-methoxyphenyl]sulfonyl]-3-methylthiourea, or a physiologically acceptable salt of 1-[[5-[2-(5-chloro-2-methoxybenzamido)ethyl]-2-methoxyphenyl]sulfonyl]-3-methylthiourea, 1-[[5-[2-(5-chloro-2-methoxybenzamido)ethyl]-2-(2-methoxyethoxy)phenyl]sulfonyl]-3-methylthiourea, or 1-[[5-[2-(5-tert-butyl-2-methoxybenzamido)ethyl]-2-methoxyphenyl]sulfonyl]-3-methylthiourea.

8. A method as claimed in claim 1, which comprises administering a sodium salt of a benzenesulfonyl(thio)urea of the formula I.

9. A method as claimed in claim 1, wherein the disfunction of the autonomous nervous system is a vagal disfunction.

10. A method as claimed in claim 1, wherein the disfunction of the autonomous nervous system is a vagal disfunction of the heart.

11. A method as claimed in claim 1, wherein the disfunction of the autonomous nervous system is a vagal disfunction of the heart in the case of coronary heart disease, angina pectoris, cardiac infarction, postmyocardial infarction, cardiac insufficiency, cardiomyopathy or diabetes mellitus.

12. A method as claimed in claim 1, which comprises administering the beta-receptor blocker alprenolol, oxprenolol, penbutolol, bupranolol, metoprolol, betaxolol, atenolol, acebutolol, metipranolol, propranolol, nadolol, pindolol, mepindolol, carteolol, timolol, sotalol, carvedilol, bisoprolol, celiprolol, carazolol, talinolol, tertatolol, or bopindolol, or a physiologically acceptable salt of alprenolol, oxprenolol, penbutolol, bupranolol, metoprolol, betaxolol, atenolol, acebutolol, metipranolol, propranolol, nadolol, pindolol, mepindolol, carteolol, timolol, sotalol, carvedilol, bisoprolol, celiprolol, carazolol, talinolol, tertatolol, or bopindolol.

13. A kit for the treatment or prophylaxis of a disfunction of the autonomous nervous system, which comprises a benzenesulfonyl(thio)urea of the formula I or a physiologically acceptable salt thereof, in any stereoisomeric form, or a mixture of benzenesulfonyl(thio)ureas of the formula I or physiologically acceptable salts thereof, in any stereoisomeric forms, in which R¹ is hydrogen, methyl or trifluoromethyl;

R² is hydrogen, halogen, $(C_1–C_6)$-alkyl, $(C_1–C_6)$-alkoxy, $(C_1–C_6)$-alkoxy-$(C_1–C_4)$-alkoxy-, $(C_1–C_6)$-alkoxy—$(C_1–C_4)$-alkoxy-$(C_1–C_4)$-alkoxy-, $(C_1–C_6)$-alkylthio, $(C_1–C_6)$-fluoroalkoxy or $(C_1–C_6)$-fluoroalkyl;

E is oxygen or sulfur;

Y is a hydrocarbon residue of the formula —$(CR^3_2)_n$— in which the residues $R^3$ independently of one another are each hydrogen or $(C_1–C_2)$-alkyl and n is 1, 2, 3 or 4;

X is hydrogen, halogen or $(C_1–C_6)$-alkyl;

Z is halogen, nitro, $(C_1–C_4)$-alkoxy or $(C_1–C_4)$-alkyl; and a beta-receptor blocker or physiologically acceptable salt thereof, for simultaneous, separate or sequential administration with the benzenesulfonyl(thio)urea of the formula I, physiologically acceptable salt of the benzenesulfonyl(thio)urea of the formula I, or mixture thereof.

14. A pharmaceutical preparation, comprising a benzenesulfonyl(thio)urea of the formula I or a physiologically acceptable salt thereof,

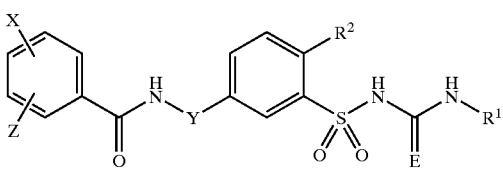

in any stereoisomeric form, or
a mixture of benzenesulfonyl(thio)ureas of the formula I or physiologically acceptable salts thereof, in any stereoisomeric forms,
in which
$R^1$ is hydrogen, methyl or trifluoromethyl;
$R^2$ is hydrogen, halogen, $(C_1-C_6)$-alkyl, $(C_1-C_6)$-alkoxy, $(C_1-C_6)$-alkoxy-$(C_1-C_4)$-alkoxy-, $(C_1-C_6)$-alkoxy$(C_1-C_4)$-alkoxy$(C_1-C_4)$-alkoxy-, $(C_1-C_6)$-alkylthio, $(C_{1-C6})$-fluoroalkoxy or $(C_1-C_6)$-fluoroalkyl;
E is oxygen or sulfur;
Y is a hydrocarbon residue of the formula $-(CR^3{}_2)_n-$ in which the residues $R^3$ independently of one another are each hydrogen or $(C_1-C_2)$-alkyl and n is 1, 2, 3 or 4;
X is hydrogen, halogen or $(C_1-C_6)$-alkyl;
Z is halogen, nitro, $(C_1-C_4)$-alkoxy or $(C_1-C_4)$-alkyl; and
at least one beta-receptor blocker or physiologically acceptable salt thereof; and a physiologically acceptable carrier.

15. A pharmaceutical preparation as claimed in claim 14, which comprises 1-[[5-[2-(5-chloro-2-methoxybenzamido)ethyl]-2-methoxyphenyl]sulfonyl]-3-methylthiourea, 1-[[5-[2-(5-chloro-2-methoxybenzamido)ethyl]-2-(2-methoxyethoxy)phenyl]sulfonyl]-3-methylthiourea, or 1-[[5-[2-(5-tert-butyl-2-methoxybenzamido)ethyl]-2-methoxyphenyl]sulfonyl]-3-methylthiourea, or a physiologically acceptable salt of 1-[[5-[2-(5-chloro-2-methoxybenzamido)ethyl]-2-methoxyphenyl]sulfonyl]-3-methylthiourea, I -[[5-[2-(5-chloro-2-methoxybenzamido)ethyl]-2-(2-methoxyethoxy)phenyl]sulfonyl]-3-methylthiourea, or 1-[[5-[2-(5-tert-butyl-2-methoxybenzamido)ethyl]-2-methoxyphenyl]sulfonyl]-3-methylthiourea.

16. A pharmaceutical preparation as claimed in claim 14, which comprises at least one sodium salt of the compound of the formula I.

17. A pharmaceutical preparation as claimed in claim 14, which comprises the beta-receptor blocker alprenolol, oxprenolol, penbutolol, bupranolol, metoprolol, betaxolol, atenolol, acebutolol, metipranolol, propranolol, nadolol, pindolol, mepindolol, carteolol, timolol, sotalol, carvedilol, bisoprolol, celiprolol, carazolol, talinolol, tertatolol, or bopindolol, or a physiologically acceptable salt of alprenolol, oxprenolol, penbutolol, bupranolol, metoprolol, betaxolol, atenolol, acebutolol, metipranolol, propranolol, nadolol, pindolol, mepindolol, carteolol, timolol, sotalol, carvedilol, bisoprolol, celiprolol, carazolol, talinolol, tertatolol, or bopindolol.

18. 1-[[5-[2-(5-tert-Butyl-2-methoxybenzamido)ethyl]-2-methoxyphenyl]sulfonyl]-3-methylthiourea or a physiologically acceptable salt thereof.

19. 1-[[5-[2-(5-tert-Butyl-2-methoxybenzamido)ethyl]-2-methoxyphenyl]sulfonyl]-3-methylurea or a physiologically acceptable salt thereof.

20. 1-[[5-[2-(5-lsopropyl-2-methoxybenzamido)ethyl]-2-methoxyphenyl]sulfonyl]-3-methylthiourea or a physiologically acceptable salt thereof.

21. 1-[[5-[2-(5-tert-Butyl-2-methoxybenzamido)ethyl]-2-(2-5 methoxyethoxy)phenyl]sulfonyl]-3-methylthiourea or a physiologically acceptable salt thereof.

22. 1-[[5-[2-(5-tert-Butyl-2-methoxybenzamido)ethyl]-2-methoxyphenyl]sulfonyl]-3-methylthiourea sodium salt.

23. A pharmaceutical preparation, comprising a compound of claim 18 and a physiologically acceptable carrier.

24. A pharmaceutical preparation, comprising a compound of claim 19 and a physiologically acceptable carrier.

25. A pharmaceutical preparation, comprising a compound of claim 20 and a physiologically acceptable carrier.

26. A pharmaceutical preparation, comprising a compound of claim 21 and a physiologically acceptable carrier.

27. A pharmaceutical preparation, comprising the compound of claim 22 and a physiologically acceptable carrier.

28. A kit as claimed in claim 14, which comprises 1-[[5-[2-(5-chloro-2-methoxy-benzamido)ethyl]-2-methoxyphenyl]sulfonyl]-3-methylthiourea, 1-[[5-[2-(5-chloro-2-methoxybenzamido)ethyl]-2-(2-methoxyethoxy)phenyl]sulfonyl]-3-methylthiourea, or 1-[[5-[2-(5-tert-butyl-2-methoxybenzamido)ethyl]-2-methoxyphenyl]sulfonyl]-3-methylthiourea, or a physiologically acceptable salt of 1-[[5-[2-(5-chloro-2-methoxy-benzamido)ethyl]-2-methoxyphenyl]sulfonyl]-3-methylthiourea, 1-[[5-[2-(5-chloro-2-methoxybenzamido)ethyl]-2-(2-methoxyethoxy)phenyl]sulfonyl]-3-methylthiourea, or 1-[[5-[2-(5-tert-butyl-2-methoxybenzamido)ethyl]-2-methoxyphenyl]sulfonyl]-3-methylthiourea.

29. A kit as claimed in claim 13, which comprises at least one sodium salt of the compound of the formula I.

30. A kit as claimed in claim 13, which comprises the beta-receptor blocker alprenolol, oxprenolol, penbutolol, bupranolol, metoprolol, betaxolol, atenolol, acebutolol, metipranolol, propranolol, nadolol, pindolol, mepindolol, carteolol, timolol, sotalol, carvedilol, bisoprolol, celiprolol, carazolol, talinolol, tertatolol, or bopindolol, or a physiologically acceptable salt of alprenolol, oxprenolol, penbutolol, bupranolol, metoprolol, betaxolol, atenolol, acebutolol, metipranolol, propranolol, nadolol, pindolol, mepindolol, carteolol, timolol, sotalol, carvedilol, bisoprolol, celiprolol, carazolol, talinolol, tertatolol, or bopindolol.

* * * * *

UNITED STATES PATENT AND TRADEMARK OFFICE
CERTIFICATE OF CORRECTION

PATENT NO.    : 6,414,030 B1  
DATED         : July 2, 2002  
INVENTOR(S)   : Wirth et al.

It is certified that error appears in the above-identified patent and that said Letters Patent is hereby corrected as shown below:

<u>Title page, Item [54] and Column 1, line 6,</u>  
Title, "BETA-RECEPTORS" should read -- BETA-RECEPTOR --.

<u>Column 26,</u>  
Line 55, "($C_1$-$C_6$-fluoroalkoxy" should read -- ($C_1$-$C_6$)-fluoroalkoxy --.

<u>Column 27,</u>  
Line 14, "($C_1$-$C_6$-fluoroalkoxy" should read -- ($C_1$-$C_6$)-fluoroalkoxy --.  
Line 23, "($C_1$-C6)-alkyl" should read -- ($C_1$-$C_6$)-alkyl --.  
Line 54, "[2(5-chloro-2-methoxybenzamido)ethyl]" should read -- [2-(5-chloro-2-methoxybenzamido)ethyl] --.

<u>Column 29,</u>  
Line 19, "alkoxy($C_1$-$C_4$)-alkoxy($C_1$-$C_4$)-alkoxy-" should read -- alkoxy-($C_1$-$C_4$)-alkoxy-($C_1$-$C_4$)-alkoxy- --.  
Line 20, "($C_1$-$_{C6}$-fluoroalkoxy" should read -- ($C_1$-$C_6$)-fluoroalkoxy --.  
Line 41, "I -[[5-[2-(5-chloro-2-methoxybenzamido)" should read -- 1-[[5-[2-(5-chloro-2-methoxybenzamido) --.

<u>Column 30,</u>  
Line 11, "lsopropyl" should read -- Isopropyl --.  
Line 29, "claim 14" should read -- claim 13 --.  
Line 36, "methoxy-benzamido" should read -- methoxybenzamido --.

Signed and Sealed this

Twelfth Day of November, 2002

*Attest:*

JAMES E. ROGAN  
*Director of the United States Patent and Trademark Office*

*Attesting Officer*